United States Patent
Han et al.

(10) Patent No.: US 11,683,955 B2
(45) Date of Patent: Jun. 20, 2023

(54) LIGHT ABSORBER AND ORGANIC ELECTROLUMINESCENCE DEVICE INCLUDING THE SAME

(71) Applicant: SAMSUNG DISPLAY CO., LTD., Yongin-si (KR)

(72) Inventors: Sanghyun Han, Yongin-si (KR); Jongwoo Kim, Yongin-si (KR); Eunjae Jeong, Yongin-si (KR); Youngkook Kim, Yongin-si (KR); Seokhwan Hwang, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 1160 days.

(21) Appl. No.: 16/044,781

(22) Filed: Jul. 25, 2018

(65) Prior Publication Data
US 2019/0036080 A1    Jan. 31, 2019

(30) Foreign Application Priority Data
Jul. 26, 2017    (KR) ........................ 10-2017-0094881

(51) Int. Cl.
*H10K 50/85* (2023.01)
*H10K 50/84* (2023.01)
(Continued)

(52) U.S. Cl.
CPC ........ *H01L 51/5262* (2013.01); *C07D 307/91* (2013.01); *C07D 333/76* (2013.01);
(Continued)

(58) Field of Classification Search
CPC ............ H01L 51/5253; H01L 51/5278; C07D 307/91; C07D 333/76; C07D 409/12
See application file for complete search history.

(56) References Cited

U.S. PATENT DOCUMENTS 6,337,492 B1 * 1/2002 Jones .................. H01L 27/3204
257/40
9,293,712 B2    3/2016 Kwong et al.
(Continued)

FOREIGN PATENT DOCUMENTS

CN    103543607 A    1/2014
CN    106146538 A    11/2016
(Continued)

OTHER PUBLICATIONS

Ito et al., Machine translation of WO-2013039184-A1 (2013) pp. 1-103. (Year: 2013).*
(Continued)

*Primary Examiner* — Dylan C Kershner
(74) *Attorney, Agent, or Firm* — Lewis Roca Rothgerber, Christie LLP

(57) ABSTRACT

Provided are a light absorber represented by Formula 1 and an organic electroluminescence device including a light
(Continued)

absorption layer including the light absorber:

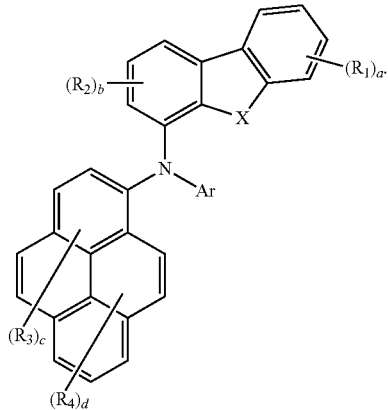

[Formula 1]

In Formula 1, $X_1$ is O or S.

13 Claims, 4 Drawing Sheets

(51) Int. Cl.
    *H10K 50/844*     (2023.01)
    *C07D 333/76*     (2006.01)
    *C07D 409/12*     (2006.01)
    *C07D 307/91*     (2006.01)
    *H10K 50/86*     (2023.01)
    *H01L 51/52*     (2006.01)

(52) U.S. Cl.
    CPC .......... *C07D 409/12* (2013.01); *H01L 51/524* (2013.01); *H01L 51/5253* (2013.01); *H01L 51/5256* (2013.01); *H01L 51/5284* (2013.01)

(56) References Cited

U.S. PATENT DOCUMENTS

| | | | |
|---|---|---|---|
| 9,461,272 B2 | 10/2016 | Yang | |
| 2001/0000005 A1* | 3/2001 | Forrest | H01L 51/5234 204/192.12 |
| 2010/0244073 A1 | 9/2010 | Ito et al. | |
| 2011/0248246 A1 | 10/2011 | Ogita et al. | |
| 2012/0138918 A1* | 6/2012 | Naraoka | H05B 33/14 257/40 |
| 2013/0089724 A1 | 4/2013 | Poncelet et al. | |
| 2014/0014928 A1* | 1/2014 | Okumura | C08G 8/24 257/40 |

FOREIGN PATENT DOCUMENTS

| | | | | |
|---|---|---|---|---|
| CN | 106316926 A | 1/2017 | | |
| CN | 106565705 A | 4/2017 | | |
| CN | 111662258 A | 9/2020 | | |
| JP | 2002-184572 A | 6/2002 | | |
| KR | 10-2010-0053533 A | 5/2010 | | |
| KR | 10-1030012 B1 | 4/2011 | | |
| KR | 10-2012-0080536 A | 7/2012 | | |
| KR | 10-2014-0009028 A | 1/2014 | | |
| KR | 10-2015-0004099 A | 1/2015 | | |
| KR | 10-2015-0042707 A | 4/2015 | | |
| KR | 10-2016-0081105 A | 7/2016 | | |
| KR | 10-2016-0142915 A | 12/2016 | | |
| WO | WO-2011043083 A1 * | 4/2011 | ......... | H01L 51/5253 |
| WO | WO-2013039184 A1 * | 3/2013 | ........... | C07D 307/91 |

OTHER PUBLICATIONS

Ghosh et al., "Thin-film encapsulation of organic lightemitting devices" Applied Physics Letters. 86, 223503 pp. 1-3 (2005). (Year: 2005).*

Chinese Office Action dated Sep. 28, 2022, and Search Report dated Sep. 22, 2022, of the corresponding Chinese Application No. 201810768848.7, 6 pages.

STN-Registry: RN 1427556-66-8, Apr. 9, 2013.

* cited by examiner

LIGHT ABSORBER AND ORGANIC ELECTROLUMINESCENCE DEVICE INCLUDING THE SAME

CROSS-REFERENCE TO THE RELATED APPLICATION

Korean Patent Application No. 10-2017-0094881, filed on Jul. 26, 2017, in the Korean Intellectual Property Office, and entitled: "Light Absorber and Organic Electroluminescence Device Including the Same," is incorporated by reference herein in its entirety.

BACKGROUND

1. Field

Embodiments relate to a light absorber and an organic electroluminescence device including the same.

2. Description of the Related Art

The development of an organic electroluminescence display as an image display is being actively conducted. The organic electroluminescence display is different from a liquid crystal display and is a so called self-luminescent display accomplishing displays via the recombination of holes and electrons injected from a first electrode and a second electrode in an emission layer and via light emission from a luminescent material including an organic compound in the emission layer.

As an organic electroluminescence device, an organic device may include. for example, a first electrode, a hole transport layer provided on the first electrode. an emission layer provided on the hole transport layer, an electron transport layer provided on the emission layer, and a second electrode provided on the electron transport layer. Holes are injected from the first electrode, and the injected holes move via the hole transport layer and are injected into the emission layer. Meanwhile, electrons are injected from the second electrode, and the injected electrons move via the electron transport layer and are injected into the emission layer. The holes and electrons injected into the emission layer recombine to produce excitons in the emission layer. The organic electroluminescence device emits light using light generated by the transition of the excitons to a ground state.

SUMMARY

Embodiments are directed to a light absorber represented by the following Formula 1:

[Formula 1]

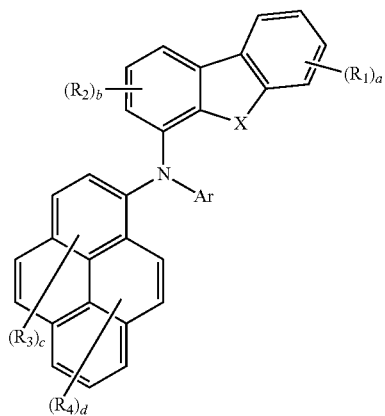

In Formula 1, X is O or S, Ar is a substituted or unsubstituted aryl group having 6 to 30 carbon atoms for forming a ring, a substituted or unsubstituted heteroaryl group having 2 to 30 carbon atoms for forming a ring, or a substituted or unsubstituted condensed polycyclic group having 6 to 30 carbon atoms for forming a ring. $R_1$ to $R_4$ are each independently a hydrogen atom, a deuterium atom, a substituted or unsubstituted alkyl group having 1 to 10 carbon atoms, a substituted or unsubstituted aryl group having 6 to 30 carbon atoms for forming a ring, a substituted or unsubstituted heteroaryl group having 2 to 30 carbon atoms for forming a ring, or a substituted or unsubstituted condensed polycyclic group having 6 to 30 carbon atoms for forming a ring, "a" and "c" are each independently an integer of 0 to 4, "b" is an integer of 0 to 3, and "d" is an integer of 0 to 5.

In an embodiment, Formula 1 may be represented by the following Formula 1-1:

[Formula 1-1]

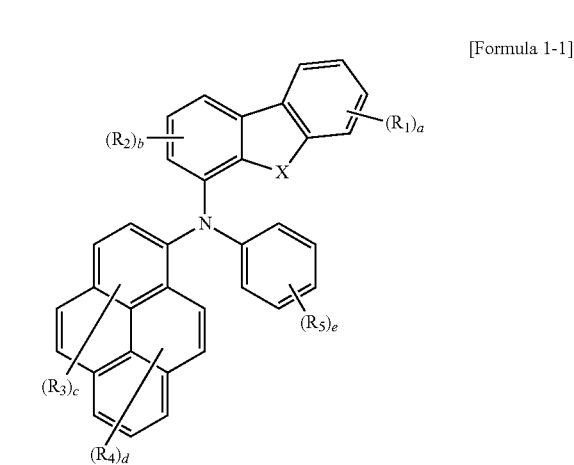

In Formula 1-1, $R_5$ is a hydrogen atom, a deuterium atom, a substituted or unsubstituted alkyl group having 1 to 10 carbon atoms, a substituted or unsubstituted aryl group having 6 to 30 carbon atoms for forming a ring, a substituted or unsubstituted heteroaryl group having 2 to 30 carbon atoms for forming a ring, or a substituted or unsubstituted condensed polycyclic group having 6 to 30 carbon atoms for forming a ring, "e" is an integer of 0 to 5, in case "e" is 2 or more. adjacent $R_5$ groups are separate or are combined with each other to form a ring, and X, $R_1$ to $R_4$, and "a" to "d" are the same as described above.

In an embodiment, Ar may be a substituted or unsubstituted phenyl group, a substituted or unsubstituted biphenyl group, a substituted or unsubstituted naphthyl group, a substituted or unsubstituted fluorene group, a substituted or unsubstituted dibenzofuran group, or a substituted or unsubstituted dibenzothiophene group.

In an embodiment, a maximum absorption wavelength may be from about 380 nm to about 410 nm.

Embodiments are also directed to an organic electroluminescence device that includes a first electrode, a hole transport region provided on the first electrode, an emission layer provided on the hole transport region, an electron transport region provided on the emission layer, a second electrode provided on the electron transport region, and a light absorption layer provided on at least one of a lower part of the first electrode or an upper part of the second electrode, wherein the light absorption layer includes a light absorber according to an embodiment.

In an embodiment, the light absorption layer may be provided on the second electrode and makes contact with the second electrode.

In an embodiment, the light absorption layer may be a thin film encapsulation layer covering the first electrode, the hole transport region, the emission layer, the electron transport region and the second electrode.

Embodiments are also directed to an organic electroluminescence device that includes a first electrode, a hole transport region provided on the first electrode, an emission layer provided on the hole transport region, an electron transport region provided on the emission layer, a second electrode provided on the electron transport region, and a light absorption layer provided on at least one of a lower part of the first electrode or an upper part of the second electrode, wherein the light absorption layer includes a pyrenyl-substituted amine compound.

In an embodiment, the pyrenyl-substituted amine compound may be further substituted with at least one of a substituted or unsubstituted dibenzofuran group or a substituted or unsubstituted dibenzothiophene group. In this case, the pyrenyl-substituted amine compound may be further substituted with a substituted or unsubstituted aryl group having 6 to 30 carbon atoms for forming a ring, a substituted or unsubstituted heteroaryl group having 2 to 30 carbon atoms for forming a ring, or a substituted or unsubstituted condensed polycyclic group having 6 to 30 carbon atoms for forming a ring.

In an embodiment, the pyrenyl-substituted amine compound may be further substituted with at least one of a substituted or unsubstituted dibenzofuran group or a substituted or unsubstituted dibenzothiophene group. In this case, the pyrenyl-substituted amine compound may be further substituted with a substituted or unsubstituted phenyl group, a substituted or unsubstituted biphenyl group, a substituted or unsubstituted naphthyl group, a substituted or unsubstituted fluorene group, a substituted or unsubstituted dibenzofuran group, or a substituted or unsubstituted dibenzothiophene group.

BRIEF DESCRIPTION OF THE DRAWINGS

Features will become apparent to those of skill in the art by describing in detail example embodiments with reference to the attached drawings in which.

DETAILED DESCRIPTION

Figure 1:
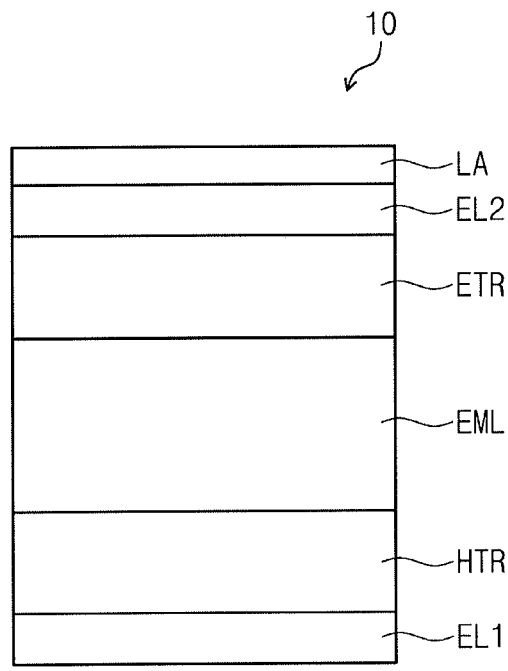
FIG. 1 is a cross-sectional view schematically illustrating an organic electroluminescence device according to an example embodiment.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey example implementations to those skilled in the art. In the drawing figures, the dimensions of layers and regions may be exaggerated for clarity of illustration. Like reference numerals refer to like elements throughout.

It will be understood that, although the terms first, second, etc. may be used herein to describe various elements, these elements should not be limited by these terms. These terms are only used to distinguish one element from another element. For example, a first element discussed below could be termed a second element, and similarly, a second element could be termed a first element. As used herein, the singular forms are intended to include the plural forms as well, unless the context clearly indicates otherwise.

It will be further understood that the terms "comprises" or "comprising," when used in this specification, specify the presence of stated features, numerals, steps. operations, elements, parts, of a combination thereof, but do not preclude the presence or addition of one or more other features, numerals, steps, operations, elements, parts, or a combination thereof. It will also be understood that when a layer, a film, a region, a plate, etc. is referred to as being "on" another part, it can be "directly on" the other part, or intervening layers may also be present. On the contrary, when a layer, a film, a region, a plate, etc. is referred to as being "under" another part, it can be "directly under" the other part, or intervening layers may also be present.

In the present disclosure,

means a part to be connected.

In the present disclosure, "substituted or unsubstituted" may mean substituted with at least one substituent selected from the group of a deuterium atom, a halogen atom, a cyano group, a nitro group, an amino group, a silyl group, a boron group, a phosphine oxide group, a phosphine sulfide group, an alkyl group, an alkenyl group, an aryl group, and a heterocycle, or unsubstituted. In addition, each of the substituent illustrated above may be substituted or unsubstituted. For example, a biphenyl group may be interpreted as an aryl group, or a phenyl group substituted with a phenyl group.

In the present disclosure, the term "forming a ring by combining with each other" may mean forming substituted or unsubstituted cyclic hydrocarbon, or substituted or unsubstituted heterocycle by combining with each other. The cyclic hydrocarbon may include aliphatic cyclic hydrocarbon and aromatic cyclic hydrocarbon. The heterocycle may include aliphatic heterocycle and aromatic heterocycle. The cyclic hydrocarbon and heterocycle may be a monocycle or polycycle. In addition, the ring formed by combining with an adjacent group may be connected with another ring to form a spiro structure.

In the present disclosure, a halogen atom may include a fluorine atom, a chlorine atom, a bromine atom, or an iodine atom.

In the present disclosure, the alkyl group may have a linear or branched chain or a cycle shape. The carbon number of the alkyl group may be 1 to 30, 1 to 20, 1 to 10, or I to 6. Examples of the alkyl group may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldodecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyl eicosyl, 2-butyl eicosyl, 2-hexyl eicosyl, 2-octyl eicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc., without limitation.

In the present disclosure, the alkenyl group may be linear or branched. The carbon number of the alkenyl group is not specifically limited, but may be 2 to 30, 2 to 20, or 2 to 10. Examples of the alkenyl group may include vinyl, 1-butenyl, 1-pentenyl, 1,3-butadienyl aryl, styrenyl, styrylvinyl, etc., without limitation.

In the present disclosure, the aryl group means an optional functional group or substituent derived from aromatic cyclic hydrocarbon ring. The aryl group may be monocyclic aryl group or polycyclic aryl group. The carbon number of the aryl group for forming a ring may be 6 to 60, 6 to 30, 6 to 20, or 6 to 15. Examples of the aryl may include phenyl, naphthyl, fluorenyl, anthracenyl, phenanthryl, biphenyl, terphenyl, quaterphenyl, quinqphenyl, sexiphenyl, biphenylene, triphenylene, pyrenyl, benzofluoranthenyl, chrysenyl, etc., without limitation.

In the present disclosure, fluorenyl may be substituted, or two substituents may be combined with each other to form a spiro structure. Examples of the substituted fluorenyl are as follows. However, an example embodiment is not limited thereto.

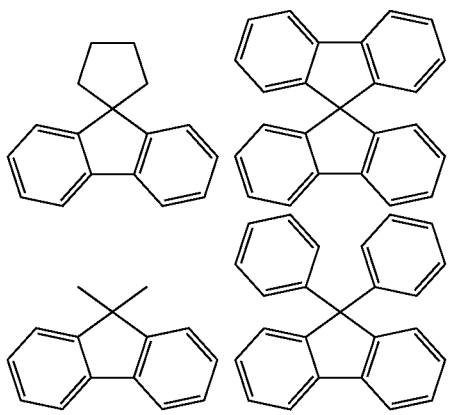

In the present disclosure, the heteroaryl may be heteroaryl group including at least one of O, N, P, Si or S as a heteroatom. When the heteroaryl group includes two heteroatoms, two heteroatoms may be the same or different from each other. The carbon number of the heteroaryl group for forming a ring may be 2 to 60, 2 to 30, or 2 to 20. The heteroaryl group may be monocyclic heteroaryl group or polycyclic heteroaryl group. The heteroaryl group may have a structure, for example of two rings or three rings. Examples of the heteroaryl may include thiophene, furan, pyrrole, imidazole, thiazole, oxazole, oxadiazole, triazole, pyridyl, bipyridyl, pyrimidyl, triazine, triazole, acridyl, pyridazine, pyrazinyl, quinolinyl, quinazoline, quinoxalinyl, phenoxazyl, phthalazinyl, pyrido pyrimidinyl, pyrido pyrazinyl, pyrazino pyrazinyl, isoquinoline, indole, carbazole, N-arylcarbazole, N-heteroaryl carbazole. N-alkyl carbazole, benzoxazole, benzoimidazole, benzothiazole, benzocarbazole, benzothiophene, dibenzothiophene, thienothiophene, benzofuranyl, phenanthroline, thiazolyl, isooxazolyl, oxadiazolyl, thiadiazolyl, benzothiazolyl, phenothiazinyl, dibenzosilole, dibenzofuranyl, etc., without limitation.

In the present disclosure, the condensed polycyclic group means a structure not corresponding to an aryl group and a heteroaryl group among a polycyclic group.

In the present disclosure, the silyl group may include alkylsilyl group and arylsilyl group. Examples of the silyl group may include trimethylsilyl, triethylsilyl, t-butyldimethylsilyl, vinyldimethylsilyl, propyldimethylsilyl, triphenylsilyl, diphenylsilyl, phenylsilyl, etc., without limitation.

In the present disclosure, the boron group may include alkyl boron group and aryl boron group. Examples of the boron group may include trimethylboron, triethylboron, t-butyldimethyl boron, triphenylboron, diphenylboron, phenylboron, etc., without limitation.

In the present disclosure, the carbon number of the amino group is not specifically limited, but may be 1 to 30. The amino group may include an alkylamino group and an acylamino group. Examples of the amino group may include a methylamino group, a dimethylamino group, a phenylamino group, a diphenylamino group, a naphthylamino group, a 9-methyl-anthracenylamino group, a triphenylamino group, etc., without limitation.

In the present disclosure, a phosphine oxide group may be substituted with, for example, at least one of an alkyl group or an aryl group. Examples of the phosphine oxide group may include a phenyl phosphine oxide group, a diphenyl phosphine oxide group, etc., without limitation.

First, the light absorber according to an example embodiment will be explained.

The light absorber according to an example embodiment is represented by Formula 1 below.

[Formula 1]

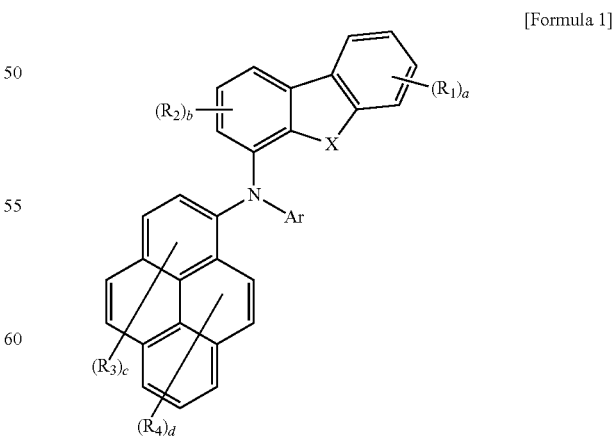

In Formula 1, X is O or S, Ar is a substituted or unsubstituted aryl group having 6 to 30 carbon atoms for forming a ring, a substituted or unsubstituted heteroaryl group having 2 to 30 carbon atoms for forming a ring, or a substituted or unsubstituted condensed polycyclic group having 6 to 30 carbon atoms for forming a ring, $R_1$ to $R_4$ are each independently a hydrogen atom, a deuterium atom, a substituted or unsubstituted alkyl group having 1 to 10 carbon atoms, a substituted or unsubstituted aryl group having 6 to 30 carbon atoms for forming a ring, a substituted or unsubstituted heteroaryl group having 2 to 30 carbon atoms for forming a ring, or a substituted or unsubstituted condensed polycyclic group having 6 to 30 carbon atoms for forming a ring, "a" and "c" are each independently an integer of 0 to 4, "b" is an integer of 0 to 3. and "d" is an integer of 0 to 5.

If "a" is 2 or more, a plurality of $R_1$ groups are the same or different.

If "b" is 2 or more, a plurality of R7 groups are the same or different.

If "c" is 2 or more, a plurality of $R_3$ groups are the same or different.

If "d" is 2 or more, a plurality of $R_4$ groups are the same or different.

For example, all "a" to "d" may be 0, in which case $R_1$ to $R_4$ are each independently a hydrogen atom. However, an example embodiment is not limited thereto, and at least one of "a" to "d" may be an integer of 1 or more.

Ar may be a substituted or unsubstituted aryl group having 6 to 20 carbon atoms for forming a ring, or a substituted or unsubstituted polycyclic heteroaryl group.

Formula 1 may be represented by, for example, Formula 1-1 below.

[Formula 1-1]

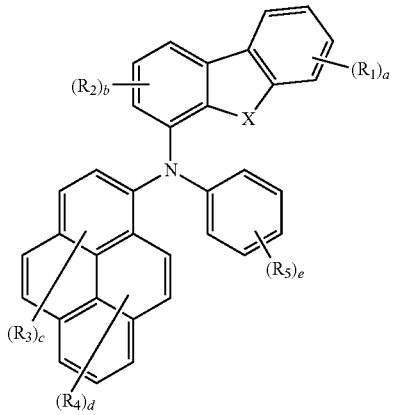

In Formula 1-1, $R_5$ is a hydrogen atom, a deuterium atom, a substituted or unsubstituted alkyl group having 1 to 10 carbon atoms, a substituted or unsubstituted aryl group having 6 to 30 carbon atoms for forming a ring, a substituted or unsubstituted heteroaryl group having 2 to 30 carbon atoms for forming a ring, or a substituted or unsubstituted condensed polycyclic group having 6 to 30 carbon atoms for forming a ring, "e" is an integer of 0 to 5, in case "e" is 2 or more, adjacent $R_5$ groups are separate or are combined with each other to form a ring. and X, $R_1$ to $R_4$, and "a" to "d" are the same as described above.

If "e" is 2 or more, a plurality of $R_5$ groups are the same or different.

"e" may be 0. However, an example embodiment is not limited thereto, and "e" may be 1, and $R_5$ may be a substituted or unsubstituted aryl group having 6 to 30 carbon atoms for forming a ring.

"e" may be 2, and adjacent two $R_5$ groups may be combined with each other to form a hydrocarbon ring or a heterocycle.

"e" may be 5, and a plurality of $R_5$ groups may be each independently a substituted or unsubstituted alkyl group having 1 to 10 carbon atoms. For example, each $R_5$ may be a substituted or unsubstituted methyl group.

In Formula 1, Ar may be represented, for example, by one of the structures below, and each of the structures may be substituted or unsubstituted.

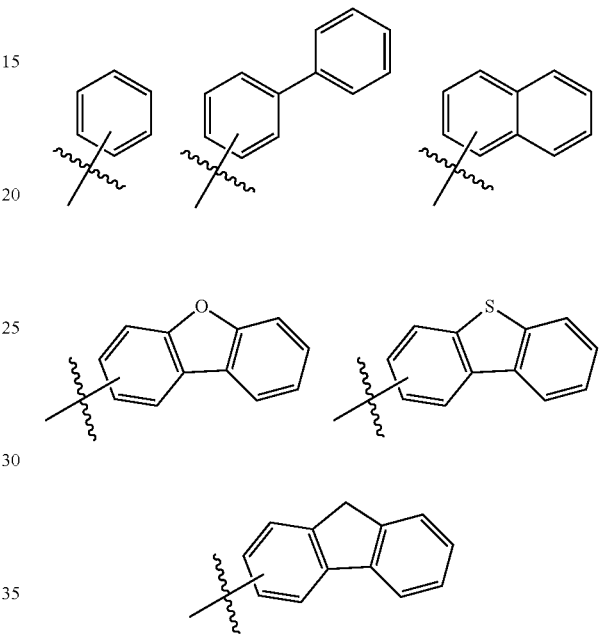

In Formula 1, Ar may be a substituted or unsubstituted phenyl group, a substituted or unsubstituted biphenyl group, a substituted or unsubstituted naphthyl group, a substituted or unsubstituted fluorene group, a substituted or unsubstituted dibenzofuran group, or a substituted or unsubstituted dibenzothiophene group.

In Formula 1. Ar may be a phenyl group which is unsubstituted or mono- or more-substituted with an alkyl group.

In Formula 1, Ar may be a fluorene group which is unsubstituted or mono- or more-substituted with an alkyl group, for example, a fluorene group which is di-substituted with methyl groups.

In Formula 1, X may be O. In Formula 1, X may be S.

The light absorber represented by Formula 1 may be a monoamine derivative.

The light absorber represented by Formula 1 may have a maximum absorption wavelength in ultraviolet rays and a portion of visible rays. As used herein, the term maximum absorption wavelength indicates a wavelength of maximum absorption.

For example, the light absorber represented by Formula 1 may have a maximum absorption wavelength of about 380 nm to about 410 nm.

The light absorber represented by Formula 1 according to an example embodiment may be selected from the compounds represented in Compound Group 1 below. However, an example embodiment is not limited thereto.

[Compound Group 1]
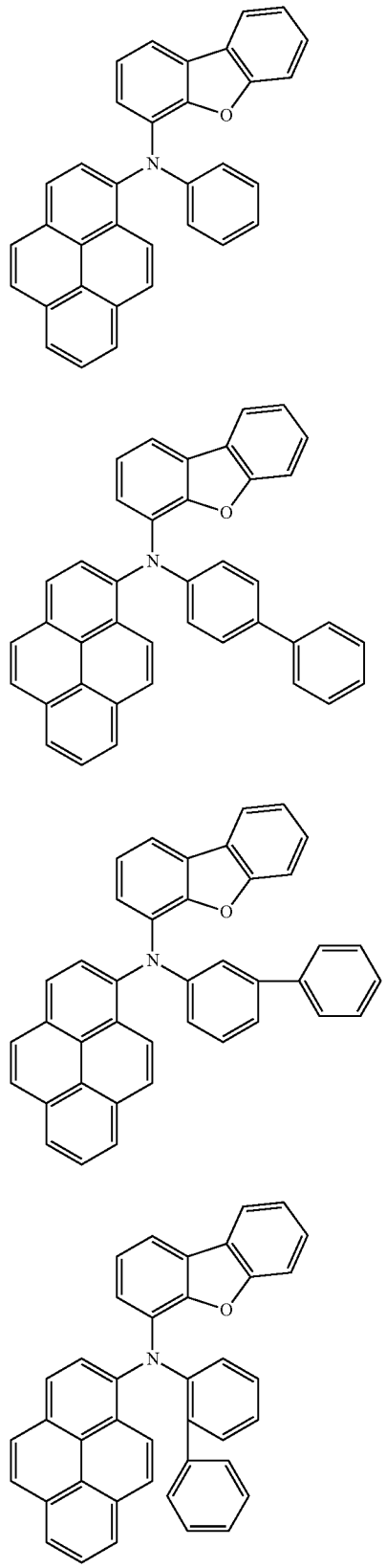
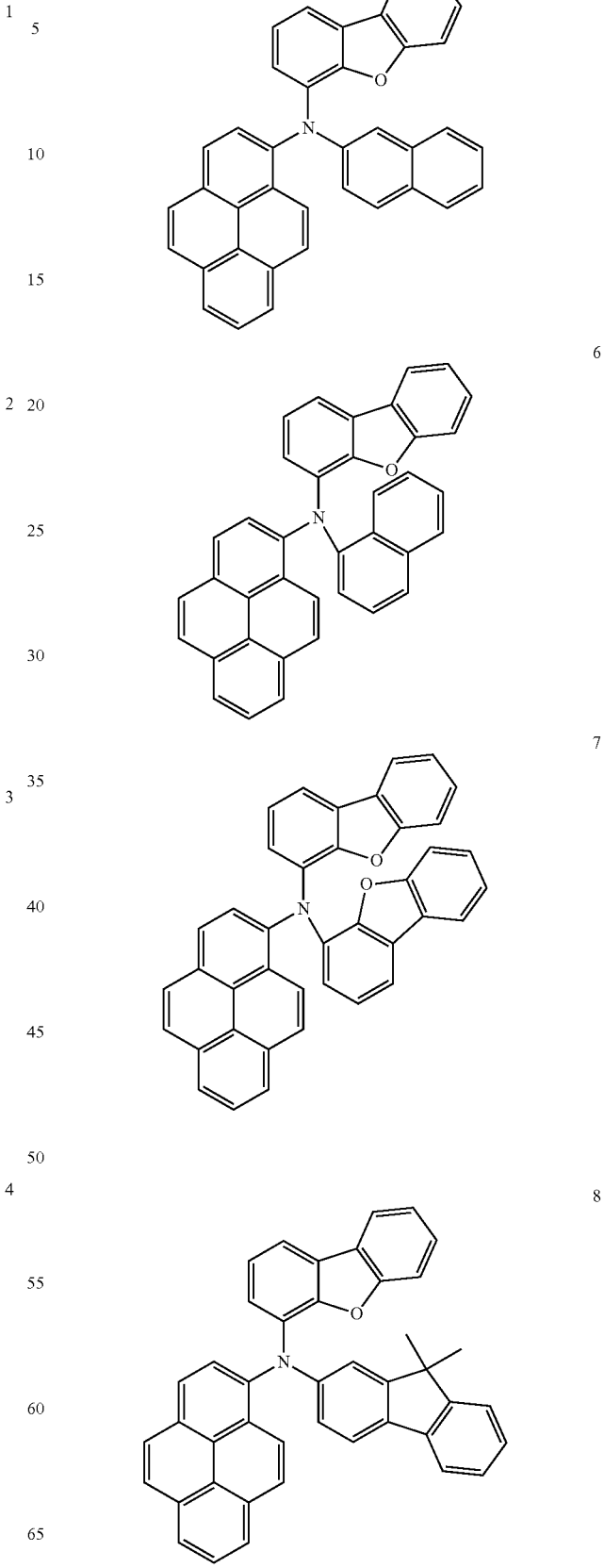

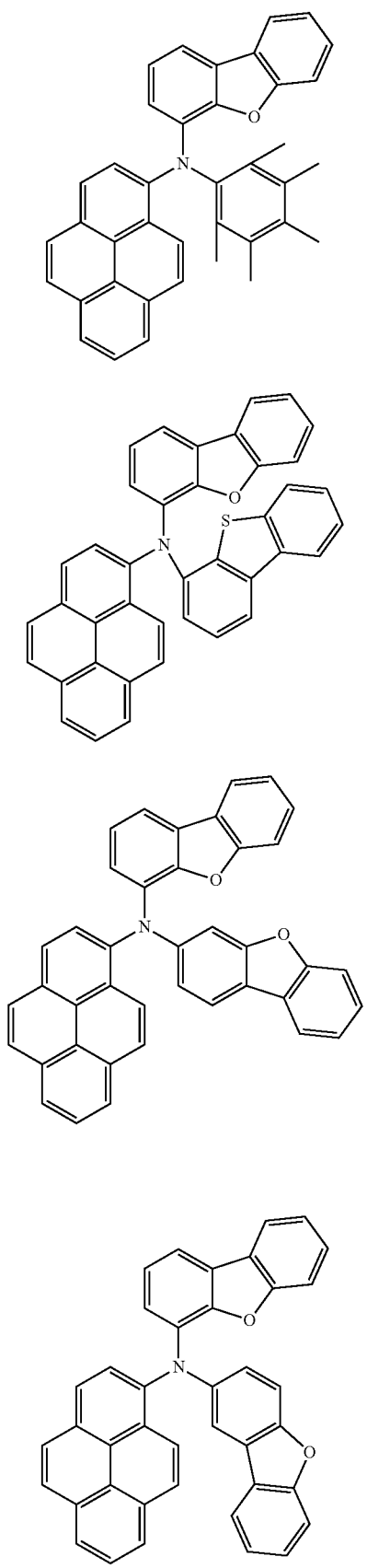
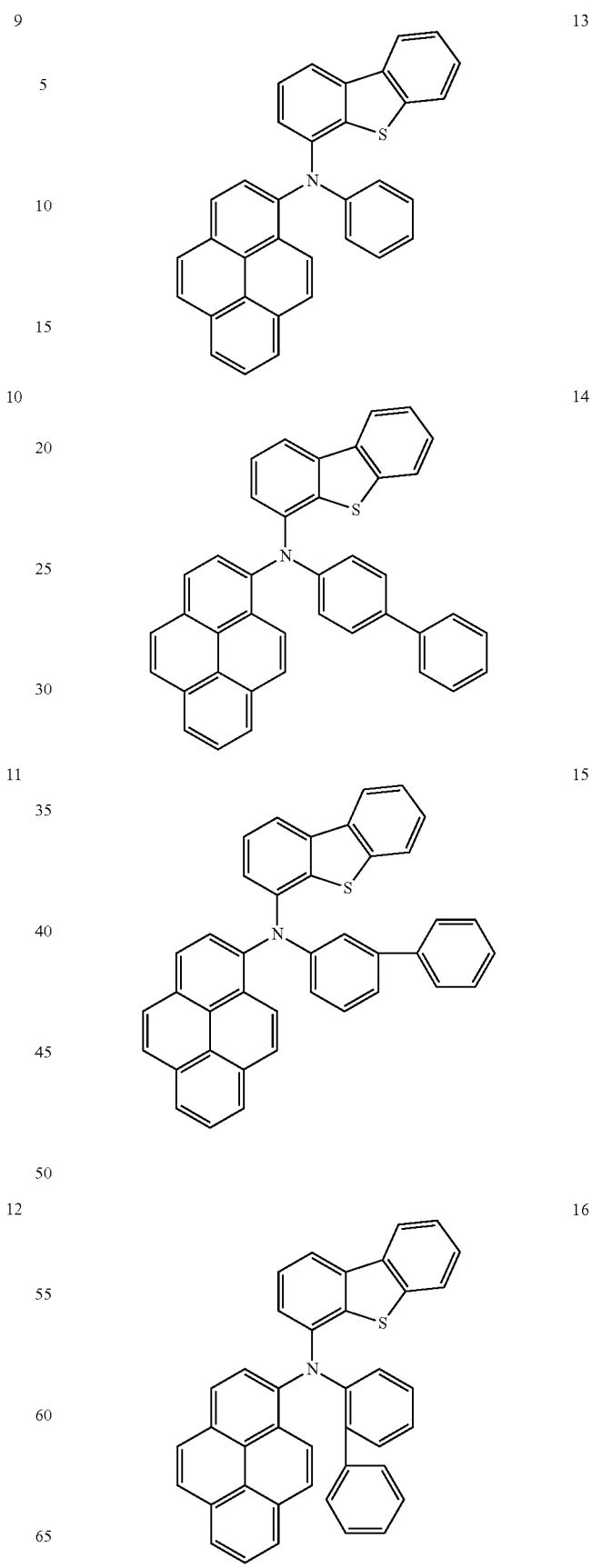

17
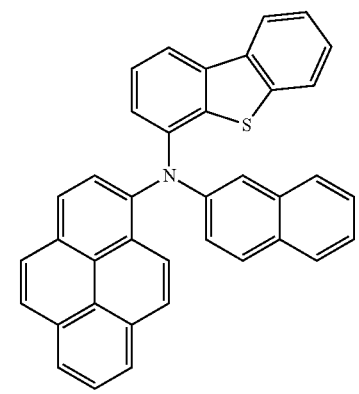

18
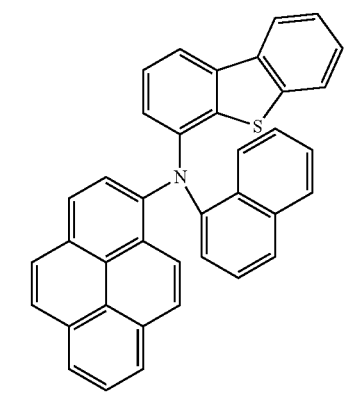

20
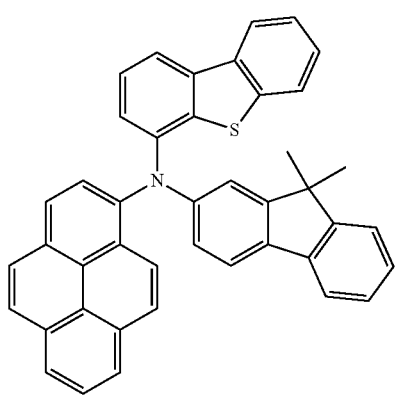

21
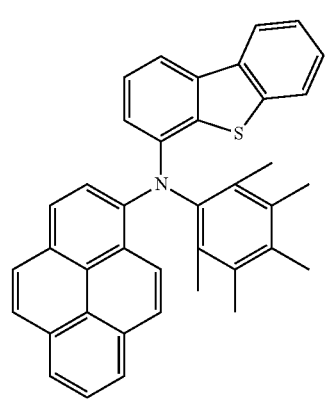

22
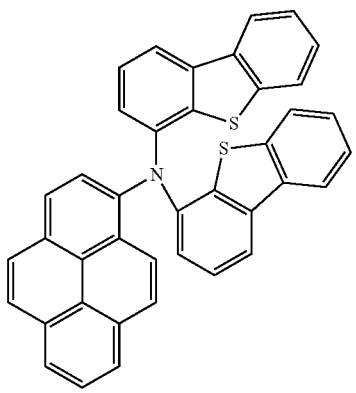

23
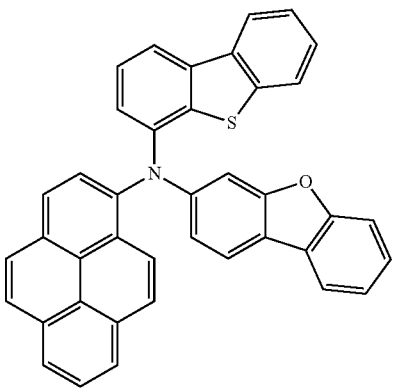

24
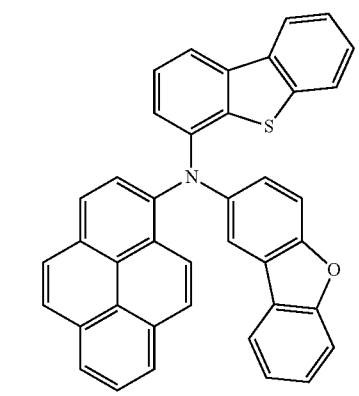

The light absorber according to an example embodiment may efficiently absorb ultraviolet rays and a portion of visible rays and has a maximum absorption wavelength of, for example, about 380 nm to about 410 nm. Accordingly, the light absorber may be applied to a part requiring the blocking of ultraviolet rays and a portion of visible rays. For example, the light absorber according to an example embodiment may be applied in an organic electroluminescence device, and may thereby prevent or minimize the deterioration of an organic layer such as an emission layer in an organic electroluminescence device due to ultraviolet rays and a portion of visible rays.

The light absorber represented by Formula 1 may be prepared based on a synthetic example which will be described below. However, the synthetic process of the light absorber represented by Formula 1 is not limited to the synthetic example which will be described below.

Hereinafter, an organic electroluminescence device according to an example embodiment will be explained. The explanation will be mainly with the difference in the light absorber according to an example embodiment, and unexplained part will follow the above-description on the light absorber according to an example embodiment.

The organic electroluminescence device according to an example embodiment includes the above-described light absorber according to an example embodiment.

Figure 2:
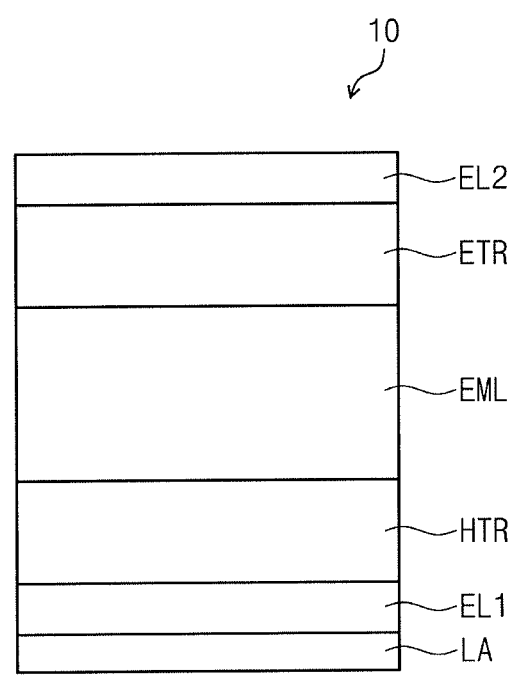
FIG. 2 is a cross-sectional view schematically illustrating an organic electroluminescence device according to an example embodiment.
Figure 3:
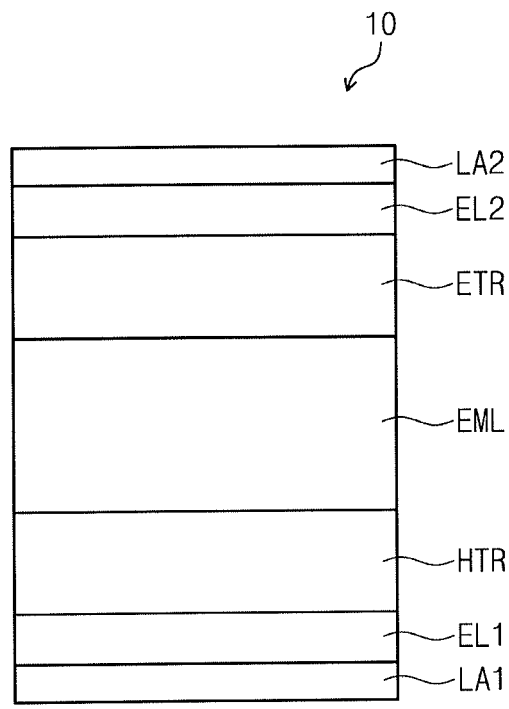
FIG. 3 is a cross-sectional view schematically illustrating an organic electroluminescence device according to an example embodiment.
Figure 4:
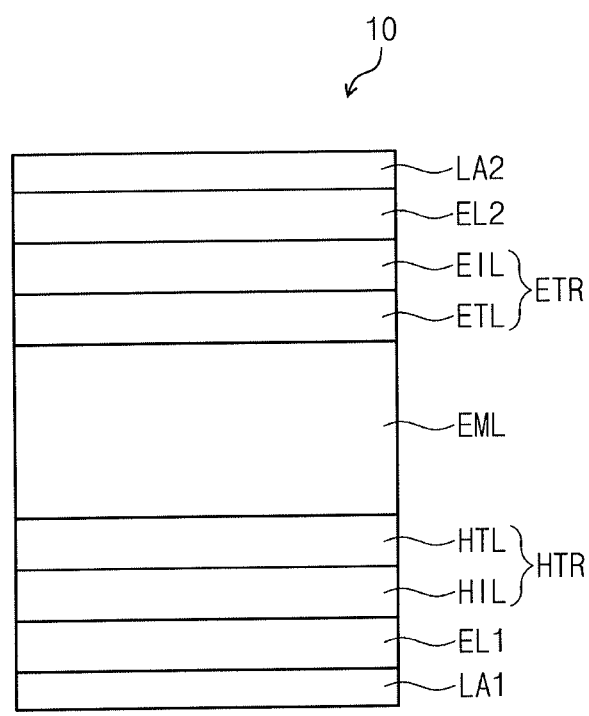
FIG. 4 is a cross-sectional view schematically illustrating an organic electroluminescence device according to an example embodiment.

FIG. 1 is a cross-sectional view schematically illustrating an organic electroluminescence device according to an example embodiment. FIG. 2 is a cross-sectional view schematically illustrating an organic electroluminescence device according to an example embodiment. FIG. 3 is a cross-sectional view schematically illustrating an organic electroluminescence device according to an example embodiment. FIG. 4 is a cross-sectional view schematically illustrating an organic electroluminescence device according to an example embodiment.

Referring to FIG. 1 to FIG. 4, an organic electroluminescence device 10 according to an example embodiment includes a first electrode EL1, a hole transport region HTR, an emission layer EML, an electron transport region ETR, a second electrode EL2, and a light absorption layer LA. The light absorption layer LA includes the above-described light absorber according to an example embodiment. For example, the light absorption layer LA includes a light absorber represented by Formula 1 below.

[Formula 1]

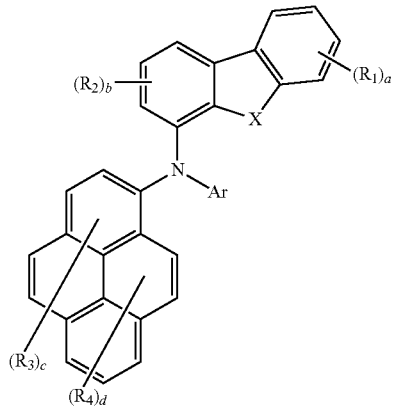

In Formula 1, particular explanation on X, Ar, $R_1$ to $R_4$, and "a" to "d" is the same as described above.

The first electrode EL1 and the second electrode EL2 are disposed facing to each other, and between the first electrode EL1 and the second electrode EL2, a plurality of organic layers may be disposed. The plurality of organic layers may include the hole transport region HTR, the emission layer EML and the electron transport region ETR.

The light absorption layer LA is provided on the lower part of the first electrode EL1 or the upper part of the second electrode EL2. FIG. 1 illustrates a case where the light absorption layer LA is provided on the upper part of the second electrode EL2, and FIG. 2 illustrates a case where the light absorption layer LA is provided on the lower part of the first electrode EL1. FIG. 3 and FIG. 4 illustrate cases where the light absorption layers LA are provided on the lower part of the first electrode EL1 and the upper part of the second electrode EL2, and in this case, the light absorption layer LA may include a first light absorption layer LA1 provided on the lower part of the first electrode EL1 and a second light absorption layer LA2 provided on the upper part of the second electrode EL2. Even not shown particularly, the light absorber according to an example embodiment may be included in another constituent element, in addition to the light absorption layer LA.

Figure 5:
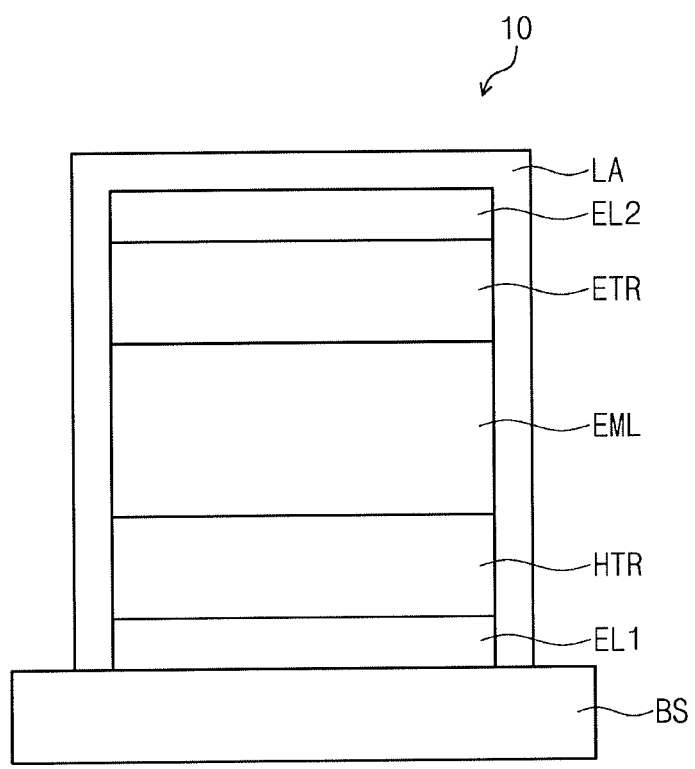
FIG. 5 is a cross-sectional view schematically illustrating an organic electroluminescence device according to an example embodiment.

FIG. 5 is a schematic cross-sectional view of an organic electroluminescence device according to an example embodiment.

Referring to FIG. 5, the light absorption layer LA may be a thin film encapsulation layer covering a first electrode EL1, a hole transport region HTR, an emission layer EML, an electron transport region ETR, and a second electrode EL2. The organic electroluminescence device 10 according to an example embodiment may further include a base substrate BS, and on one side of the base substrate BS, the first electrode EL1, the hole transport region HTR, the emission layer EML, the electron transport region ETR, and the second electrode EL2 may be provided one by one. As described above, the thin film encapsulation layer encapsulates the first electrode EL1, the hole transport region HTR, the emission layer EML, the electron transport region ETR, and the second electrode EL2 together with the base substrate BS to help prevent the penetration of oxygen and moisture into the emission layer EML, etc. If the thin film encapsulation layer is the light absorption layer LA, the penetration of ultraviolet rays and a portion of visible rays may be also prevented. In an implementation, the thin film encapsulation layer may have a multilayer structure in which at least one inorganic layer and at least one organic layer are alternately laminated, and at least one organic layer may include a light absorber represented by Formula 1. The inorganic layer may include a suitable material, for example, at least one of silicon nitride, silicon oxynitride, titanium oxide, aluminum oxide, or silicon oxide.

However, an example embodiment is not limited thereto. For example, the light absorption layer LA may be a capping layer provided on the second electrode EL2. The capping layer may further include a suitable material in addition to the light absorber according to an example embodiment. For example, α-NPD, NPB, TPD, m-MTDATA, Alq3, CuPc, N4,N4,N4',N4'-tetra(biphenyl-4-yl)biphenyl-4,4'-diamine (TPD15), 4,4',4"-tris(carbazol sol-9-yl)triphenylamine (TCTA),N,N'-bis(naphthalen-1-yl, etc., may be included. The capping layer CPL may assist in efficient emission of light emitted from the emission layer EML toward outside of the organic electroluminescence device 10.

If the organic electroluminescence device 10 according to an example embodiment includes both a capping layer and a thin film encapsulation layer, the capping layer may be provided between the second electrode EL2 and the thin film encapsulation layer, and at least one of the capping layer or the thin film encapsulation layer may include the above-described light absorber according to an example embodiment.

If the light absorption layer LA is provided on the lower part of the first electrode EL1, the light absorption layer LA may be provided between the first electrode EL1 and the base substrate BS.

The thickness of the light absorption layer LA may be, for example, from about 500 Å to about 1,000 Å.

The light absorption layer LA may further include another constituent element in addition to the light absorber according to an example embodiment, for example, an antioxidant, a binder, etc. However, an example embodiment is not limited thereto.

The light absorption layer LA may be formed using various methods such as a vacuum deposition method, a spin coating method, a cast method, a Langmuir-Blodgett (LB)

method, an inkjet printing method, a laser printing method, and a laser induced thermal imaging (LITI) method.

Hereinafter, referring to FIG. 1 to FIG. 4 again, each layer will be particularly explained.

The first electrode EL1 has conductivity. The first electrode EL1 may be a pixel electrode or an anode. The first electrode EL1 may be a transmissive electrode, a transflective electrode, or a reflective electrode. If the first electrode EL1 is the transmissive electrode, the first electrode EL1 may be formed using a transparent metal oxide such as indium tin oxide (ITO), indium zinc oxide (IZO), zinc oxide (ZnO), or indium tin zinc oxide (ITZO). If the first electrode EL1 is the transflective electrode or reflective electrode, the first electrode EL1 may include Ag, Mg. Cu, Al, Pt, Pd, Au, Ni, Nd, Ir, Cr, Li, Ca, LiF/Ca, LiF/Al. Mo, Ti, a compound thereof, or a mixture thereof (for example, a mixture of Ag and Mg). Also. the first electrode EL1 may include a plurality of layers including the reflective layer or transflective layer formed using the above materials, or a transparent layer formed using ITO, IZO, ZnO, or ITZO. For example, the first electrode EL1 may have a three-layer structure of ITO/Ag/ITO, without limitation.

The thickness of the first electrode EL1 may be from about 1,000 Å to about 10,000 Å, for example, from about 1,000 Å to about 3,000 Å.

The hole transport region HTR is provided on the first electrode EL1. The hole transport region HTR may include at least one of a hole injection layer HIL, a hole transport layer HTL, a hole buffer layer, or an electron blocking layer. The thickness of the hole transport region HTR may be, for example, from about 1,000 Å to about 1,500 Å.

The hole transport region HTR may have a single layer formed using a single material, a single layer formed using a plurality of different materials, or a multilayer structure including a plurality of layers formed using a plurality of different materials.

For example, the hole transport region HTR may have a single layer structure of a hole injection layer HIL or a hole transport layer HTL, or may have a structure of a single layer formed using a hole injection material and a hole transport material. In addition, the hole transport region HTR may have a single layer structure formed using a plurality of different materials, or a structure laminated one by one from the first electrode EL1 of hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/electron blocking layer, without limitation.

The hole transport region HTR may be formed using various methods such as a vacuum deposition method, a spin coating method, a cast method. a Langmuir-Blodgett (LB) method, an inkjet printing method, a laser printing method, and a laser induced thermal imaging (LITI) method.

The hole injection layer HIL may include, for example, a phthalocyanine compound such as copper phthalocyanine; N,N'-diphenyl-N,N'-bis-[4-(phenyl-m-tolyl-amino)-phenyl]-biphenyl-4,4'-diamine (DNTPD), 4,4',4''-tris(3-methylphenylphenylamino)triphenylamine (m-MTDATA), 4,4', 4''-tris(N,N-diphenylamino)triphenylamine (TDATA), 4,4', 4''-tris{N-(2-naphthyl)-N-phenylamino}-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(1-naphthyl)-N,N'-diphenyl-(1,1'-biphenyl)-4,4'-diamine (NPB), carbazole derivatives such as N-phenylcarbazole and polyvinyl carbazole, fluorene-based derivatives, triphenylamine-containing polyether ketone (TPAPEK), 4-isopropyl-4'-methyldiphenyliodonium tetrakis(pentafluorophenyl)borate, dipyrazino[2,3-f: 2',3'-h]quinoxaline-2,3,6,7,10,11-hexacarbonitrile (HAT-CN), etc.

The hole transport layer HTL includes, for example, carbazole derivatives such as N-phenyl carbazole and polyvinyl carbazole, fluorene-based derivatives, N,N'-bis(3-methylphenyl)-N,N'-diphenyl[1,1-biphenyl]-4,4'-diamine (TPD), triphenylamine-based derivatives such as 4,4',4''-tris (N-carbazolyl)triphenylamine (TCTA), N,N'-di(1-naphthyl)-N N'-diphenyl-(1,1'-biphenyl)-4,4'-diamine (NPB), 4,4'-cyclohexylidene bis[N,N-bis(4-methylphenyl)benzenamine] (TAPC), 4,4'-bis[N,N'-(3-tolyl)amino]-3,3'-dimethylbiphenyl (HMTPD), 1,3-bis(N-carbazolyl)benzene (mCP), etc. may be included.

The thickness of the hole transport region HTR may be from about 100 Å to about 10,000 Å, for example, from about 100 Å to about 1,000 Å. If the hole transport region HTR includes both the hole injection layer HIL and the hole transport layer HTL, the thickness of the hole injection layer HIL may be from about 100 Å to about 10,000 Å, for example, from about 100 Å to about 1,000 Å, and the thickness of the hole transport layer HTL may be from about 30 Å to about 1,000 Å. If the thicknesses of the hole transport region HTR, the hole injection layer HIL, and the hole transport layer HTL satisfy the above-described ranges, satisfactory hole transport properties may be obtained without the substantial increase of a driving voltage.

The hole transport region HTR may further include a charge generating material other than the above-described materials to improve conductivity. The charge generating material may be dispersed in the hole transport region HTR uniformly or non-uniformly. The charge generating material may be, for example, a p-dopant. The p-dopant may be one of, for example, quinone derivatives, metal oxides, or cyano group-containing compounds, without limitation. For example, non-limiting examples of the p-dopant may include quinone derivatives such as tetracyanoquinodimethane (TCNQ), and 2,3,5,6-tetrafluoro-tetracyanoquinodimethane (F4-TCNQ), metal oxides such as tungsten oxide, and molybdenum oxide, without limitation.

As described above, the hole transport region HTR may further include one of a hole buffer layer or an electron blocking layer other than the hole injection layer HIL and the hole transport layer HTL. The hole buffer layer may compensate an optical resonance distance according to the wavelength of light emitted from the emission layer EML and increase light emission efficiency. Materials included in the hole transport region HTR may be used as materials included in the hole buffer layer. The electron blocking layer is a layer helping to prevent electron injection from the electron transport region ETR to the hole transport region HTR.

The emission layer EML is provided on the hole transport region HTR. The thickness of the emission layer EML may be, for example, from about 100 Å to about 1,000 Å or about 100 Å to about 300 Å. The emission layer EML may have a single layer formed using a single material, a single layer formed using a plurality of different materials, or a multilayer structure having a plurality of layers formed using a plurality of different materials.

The emission layer EML may include a suitable material. For example, a fluorescent material including any one selected from the group of spiro-DPVBi, 2,2',7,7'-tetrakis (biphenyl-4-yl)-9,9'-spirobifluorene (spiro-6P, spiro-sexiphenyl), distyryl-benzene (DSB), distyryl-arylene (DSA), a polyfluorene (PFO)-based polymer, and a poly(p-phenylene vinylene) (PPV)-based polymer may be further included. For example, an anthracene-based compound, an arylamine-based compound or a styryl-based compound may be included. In addition, the emission layer EML may include a suitable phosphorescent material.

The emission layer EML may include a host and a dopant. The host may include a suitable material, without specific limitation, for example. tris(8-hydroxyquinolino)aluminum ($Alq_3$), 4,4'-bis(N-carbazolyl)-1,1'-biphenyl (CBP), poly(n-vinylcarbazole) (PVK), 9,10-di(naphthalene-2-yl)anthracene (ADN), 4,4',4"-tris(carbazol-9-yl)-triphenylamine (TCTA), 1,3,5-tris(N-phenylbenzimidazole-2-yebenzene (TPBi), 3-tert-butyl-9,10-di(naphth-2-yl)anthracene (TBADN), distyrylarylene (DSA). 4,4'-bis(9-carbazolyl)-2,2'-dimethyl-biphenyl (CDBP), 2-methyl-9,10-bis(naphthalen-2-yl)anthracene (MADN). bis[2-(diphenylphosphino)phenyl]ether oxide (DPEPO), hexaphenyl cyclotriphosphazene (CP1), 1,4-bis(triphenylsily)benzene (UGH2), hexaphenylcyclotrisiloxane ($DPSiO_3$), octaphenylcyclotetra siloxane ($DPSiO_4$), 2,8-bis(diphenylphosphoryl)dibenzofuran (PPF), etc.

The dopant may include, for example, styryl derivatives (for example, 1,4-bis(2-[3-N-ethylcarbazolyl]vinyl)benzene (BCzVB), 4-(di-p-tolylamino)-4'-[(di-p-tolylamino)styryl] stilbene (DPAVB), and N-(4-((E)-2-(6-((E)-4-(diphenylamino)styryl)naphthalen-2-yl)vinyl)phenyl)-N-phenyl-benzenamine (N-BDAVBi), perylene and the derivatives thereof (for example, 2,5,8,11-tetra-t-butylperylene (TBP), pyrene and the derivatives thereof (for example, 1,1-dipyrene, 1,4-dipyrenylbenzene, 1,4-bis(N,N-diphenylamino)pyrene, [bis-(1-phenylisoquinoline)iridium(III) acetylacetonate] ($Ir(ppy)_3$), $Ir(dpbic)_3$, TPD, etc.

The emission layer EML may emit phosphorescence, or fluorescence. In addition, the emission layer EML may emit thermally activated delayed fluorescence.

The emission layer may emit one of red light, green light, blue light, white light, yellow light, or cyan light.

The electron transport region ETR is provided on the emission layer EML. The electron transport region ETR may include at least one of an hole blocking layer, an electron transport layer ETL, or an electron injection layer EIL, without limitation.

The electron transport region ETR may have a single layer formed using a single material, a single layer formed using a plurality of different materials, or a multilayer structure including a plurality of layers formed using a plurality of different materials.

For example, the electron transport region ETR may have a single layer structure of an electron injection layer EIL or an electron transport layer ETL, or a single layer structure formed using an electron injection material and an electron transport material. In addition, the electron transport region ETR may have a single layer structure formed using a plurality of different materials, or a structure laminated one by one from the first electrode EL1 of electron transport layer ETL/electron injection layer EIL, or hole blocking layer/electron transport layer ETL/electron injection layer EIL, without limitation. The thickness of the electron transport region ETR may be, for example, from about 1,000 Å to about 1,500 Å.

The electron transport region ETR may be formed using various methods such as a vacuum deposition method, a spin coating method, a cast method, a Langmuir-Blodgett (LB) method, an inkjet printing method, a laser printing method, and a laser induced thermal imaging (LITI) method.

If the electron transport region ETR includes the electron transport layer ETL, the electron transport region ETR may include, for example, an anthracene-based compound. The electron transport region may include, for example, tris(8-hydroxyquinolinato)aluminum ($Alq_3$), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazolyl-1-ylphenyl)-9,10-dinaphthylanthracene, 1,3,5-tri(1-phenyl-1H-benzo[d]imidazol-2-yl)phenyl (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ). 2-(4-biphenylyl)-5-(4-tert-butylphenyl)-1,3,4-oxadiazole (tBu-PBD), bis(2-methyl-8-quinolinolato-N1.O8)-(1,1-biphenyl-4-olato) aluminum (BARIq), berylliumbis(benzoquinolin-10-olate (Bebq2), 9,10-di(naphthalene-2-yl)anthracene (ADN), or a mixture thereof, without limitation. The thickness of the electron transport layer ETL may be from about 100 Å to about 1.000 Å. for example, from about 150 Å to about 500 Å. If the thickness of the electron transport layer ETL, satisfies the above-described range, satisfactory electron transport properties may be obtained without the substantial increase of a driving voltage.

If the electron transport region ETR includes the electron injection layer EIL, the electron transport region ETR may include, for example, LiF, lithium quinolate (LiQ), $Li_2O$, BaO, NaCl, CsF, a metal in lanthanides such as Yb, or a metal halide such as RbCl and RbI, without limitation. The electron injection layer EIL may be also formed using a mixture material of an electron transport material and an insulating organo metal salt. The organo metal salt may be, for example, a material having an energy band gap of about 4 eV or more. The organo metal salt may include, for example, a metal acetate, a metal benzoate, a metal acetoacetate, a metal acetylacetonate, or a metal stearate. The thickness of the electron injection layer EIL may be from about 1 Å to about 100 Å, for example from about 3 Å to about 90 Å. If the thickness of the electron injection layer EIL satisfies the above described range, satisfactory electron injection properties may be obtained without inducing the substantial increase of a driving voltage.

The electron transport region ETR may include a hole blocking layer, as described above. The hole blocking layer may include, for example, at least one of 2,9-dimethyl-4,7-diphenyl-1,10-phenanthroline (BCP), or 4,7-diphenyl-1,10-phenanthroline (Bphen), without limitation.

The second electrode EL2 is provided on the electron transport region ETR. The second electrode EL2 may be a common electrode or a cathode. The second electrode EL2 may be a transmissive electrode, a transflective electrode or a reflective electrode. If the second electrode EL2 is the transmissive electrode, the second electrode EL2 may include a transparent metal oxide, for example, ITO, IZO, ZnO, ITZO, etc.

If the second electrode EL2 is the transflective electrode or the reflective electrode, the second electrode EL2 may include, for example, Ag, Mg, Cu, Al, Pt, Pd, Au, Ni, Nd, Ir, Cr, Li, Ca, LiF/Ca, LiF/Al, Mo, Ti, a compound including thereof, or a mixture thereof (for example, a mixture of Ag and Mg). The second electrode EL2 may have a multilayered structure including a reflective layer or a transflective layer formed using the above-described materials or a transparent conductive layer formed using ITO, IZO, ZnO, ITZO, etc.

The second electrode EL2 may be connected with an auxiliary electrode. If the second electrode EL2 is connected with the auxiliary electrode, the resistance of the second electrode EL2 may be decreased.

In the organic electroluminescence device 10, voltages are applied to each of the first electrode EL1 and the second electrode EL2, and holes injected from the first electrode EL1 move via the hole transport region HTR to the emission layer EML, and electrons injected from the second electrode EL2 move via the electron transport region ETR to the emission layer EML. The electrons and holes are recombined in the emission layer EML to generate excitons, and the excitons may emit light via transition from an excited state to a ground state.

If the organic electroluminescence device 10 is a top emission type, the first electrode EL1 may be a reflective electrode, and the second electrode EL2 may be a transmissive electrode or a transflective electrode. If the organic electroluminescence device 10 is a bottom emission type, the first electrode EL1 may be the transmissive electrode or the transflective electrode, and the second electrode EL2 may be the reflective electrode.

The organic electroluminescence device 10 according to an example embodiment provides the light absorption layer LA including the light absorber represented by Formula 1 on at least one of the lower part of the first electrode EL1 or the upper part of the second electrode EL2, and the inflow of ultraviolet rays and a portion of visible rays may be effectively prevented, which may improve stability, efficiency and life properties.

Hereinafter, an organic electroluminescence device according to another example embodiment. The explanation will be mainly with the difference in the organic electroluminescence device according to an example embodiment, and unexplained part will follow the above-description.

Referring to FIG. 1 to FIG. 5, the organic electroluminescence device 10 according to another embodiment of the present disclosure includes a first electrode EL1, a hole transport region HTR, an emission layer EML, an electron transport region ETR, a second electrode EL2, and a light absorption layer LA, and the light absorption layer LA includes a light absorber including a pyrenyl-substituted amine compound, or a monoamine derivative which is substituted with a pyrenyl group. The pyrenyl group may be substituted or unsubstituted.

The nitrogen atom of the monoamine derivative may be substituted with a substituted or unsubstituted pyrenyl group as described above, and may be further substituted with at least one of a substituted or unsubstituted dibenzofuran group or a substituted or unsubstituted dibenzothiophene group. In addition, the nitrogen atom of the monoamine derivative may be further substituted with a substituted or unsubstituted aryl group having 6 to 30 carbon atoms for forming a ring, a substituted or unsubstituted heteroaryl group having 2 to 30 carbon atoms for forming a ring, or a substituted or unsubstituted condensed polycyclic group having 6 to 30 carbon atoms for forming a ring, for example, may be further substituted with a substituted or unsubstituted phenyl group, a substituted or unsubstituted biphenyl group, a substituted or unsubstituted naphthyl group, a substituted or unsubstituted fluorene group, a substituted or unsubstituted dibenzofuran group, or a substituted or unsubstituted dibenzothiophene group.

The nitrogen atom of the monoamine derivative may be tri-substituted.

The monoamine derivative may be represented by, for example, the above-described Formula 1.

The monoamine derivative may be at least one selected from the compounds represented in the above-described Compound Group 1.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

SYNTHETIC EXAMPLES

The light absorber according to an example embodiment may be synthesized, for example, as follows. However, the synthetic method of the light absorber according to an example embodiment is not limited thereto.

1. Synthesis of Compound 2

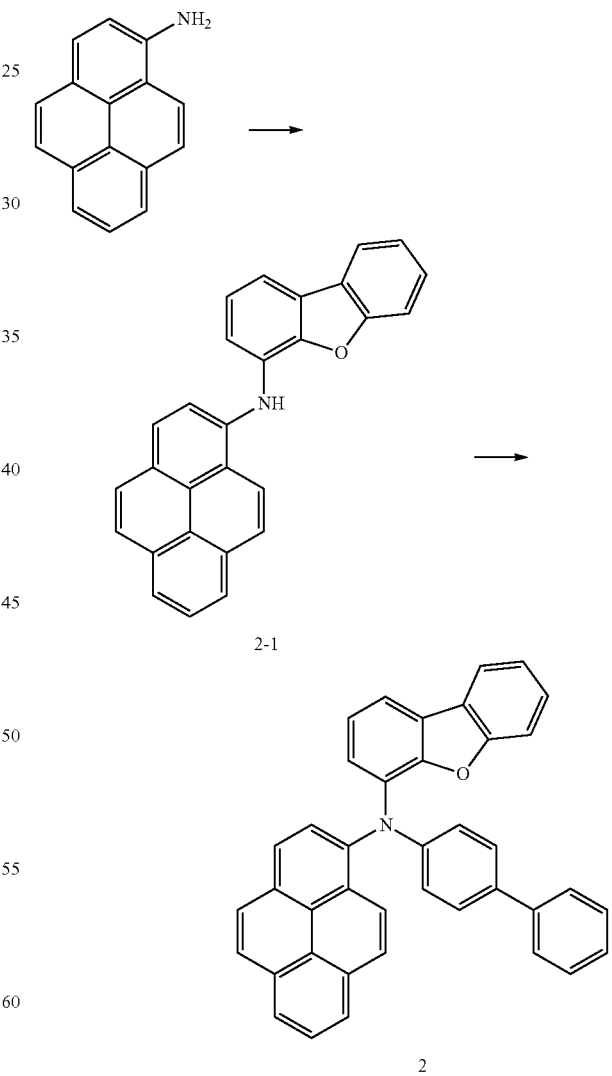

(Synthesis of Intermediate Compound 2-1)

2.171 g (10 mmol) of 1-aminopyrene, 2.471 g (10 mmol) of 4-bromodibenzofuran, 0.452 g (0.5 mmol) of tris(dibenzylideneacetone)dipalladium (Pd$_2$(dba)$_3$), 0.101 g (0.5 mmol) of PtBu$_3$, and 0.961 g (10 mmol) of NaOtBu were dissolved in 150 ml of toluene, followed by stirring at about 90° C. for about 4 hours. The reaction solution was cooled to room temperature and then, extracted with 10 ml of water and 50 ml of diethyl ether three times. The organic layer thus obtained was dried with magnesium sulfate, and residue obtained by evaporating solvents was separated by silica gel column chromatography to obtain 3.064 g (8 mmol, 8%) of Intermediate Compound 2-1.

(Synthesis of Final Compound 2)

3.210 g (6 mmol, 75%) of Final Compound 2 was synthesized by conducting the same method for synthesizing Intermediate Compound 2-1 except for using Intermediate Compound 2-1 and 4-bromobiphenyl instead of instead of 1-aminopyrene and 4-bromodibenzofuran.

2. Synthesis of Compound 5

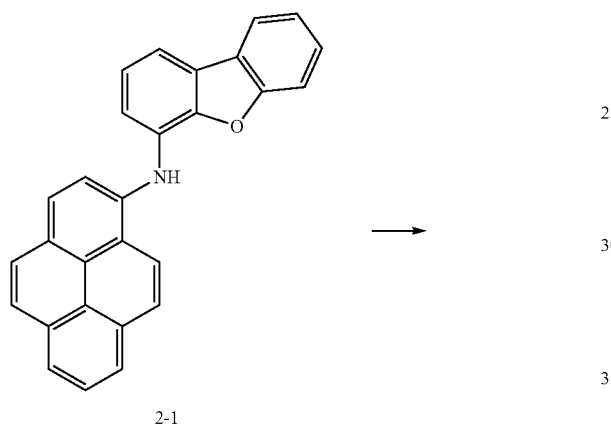

2-1

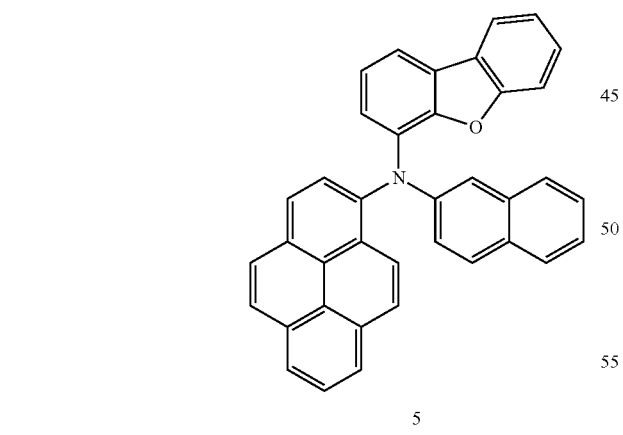

5

3.054 g (6 mmol, 75%) of Compound 5 was synthesized by conducting the same method for synthesizing Compound 2 except for using 2-bromonaphthalene instead of 4-bromobiphenyl.

3. Synthesis of Compound 10

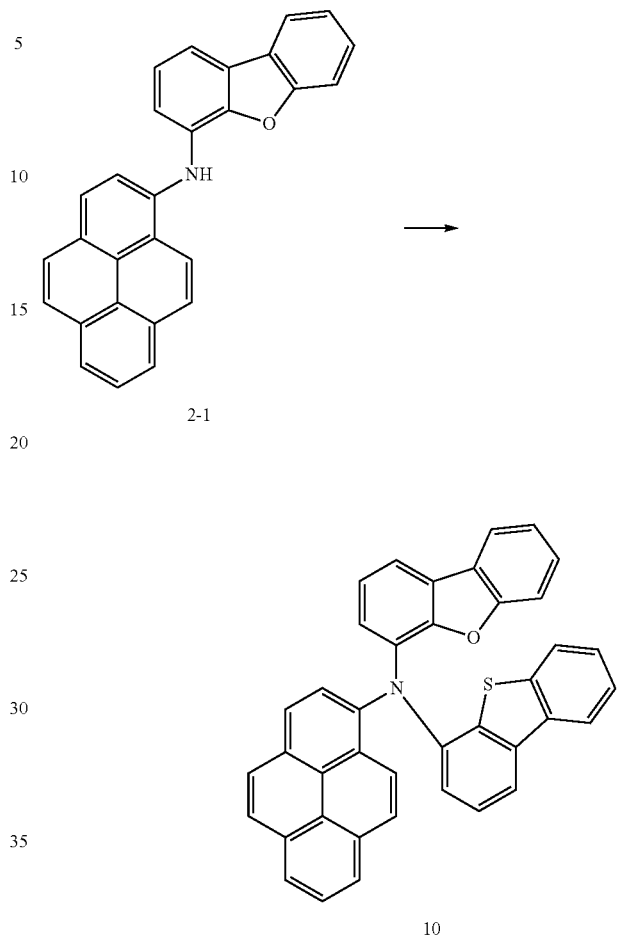

2-1

10

3.3904 g (6 mmol, 75%) of Compound 10 was synthesized by conducting the same method for synthesizing Compound 2 except for using 4-bromodibenzothiophene instead of 4-bromobiphenyl.

4. Synthesis of Compound 12

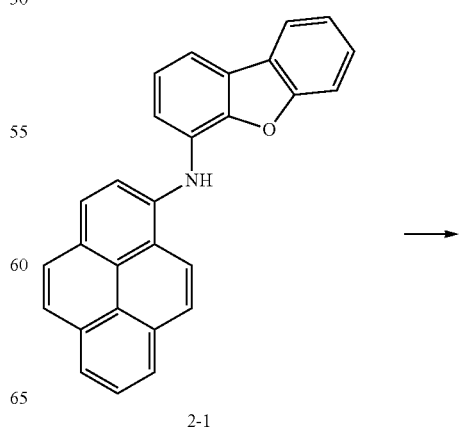

2-1

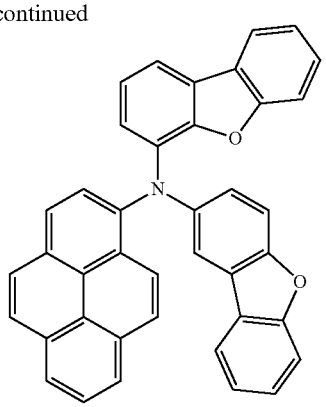

12

3.294 g (6 mmol, 75%) of Compound 12 was synthesized by conducting the same method for synthesizing Compound 2 except for using 2-bromodibenzofuran instead of 4-bromobiphenyl.

5. Synthesis of Compound 13

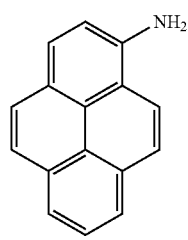

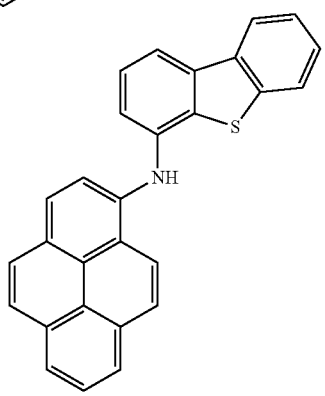

13-1

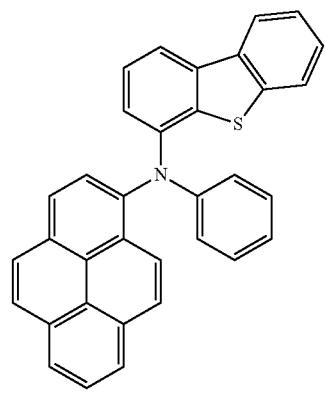

13

(Synthesis of Intermediate Compound 13-1)

3.192 g (8 mmol, 80%) of Intermediate Compound 13-1 was synthesized by conducting the same method for synthesizing Intermediate Compound 2-1 except for using 4-bromodibenzothiophene instead of 4-bromodibenzofuran.

(Synthesis of Final Compound 13)

2.850 g (6 mmol, 75%) of Compound 13 was synthesized by conducting the same method for synthesizing Compound 2 except for using Intermediate Compound 13-1 and bromobenzene instead of instead of Intermediate Compound 2-1 and 4-bromobiphenyl.

6. Synthesis of Compound 20

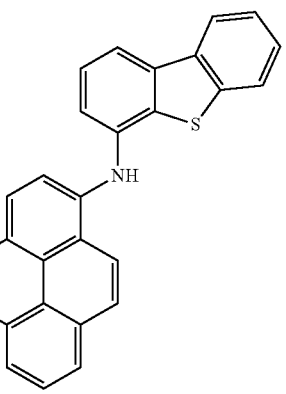

13-1

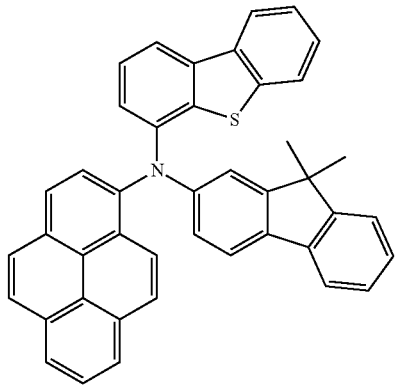

20

3.548 g (6 mmol, 75%) of Compound 20 was synthesized by conducting the same method for synthesizing Compound 13 except for using 2-dimethylfluorenerane instead of bromobenzene.

NMR and molecular weight analysis data for Compounds 2, 5, 10, 12, 13 and 20 synthesized in the synthetic examples are listed in Table 1 below.

TABLE 1
| Compound | 1H NMR (CDCl3, 300 MHz) | LC/MS found | calc. |
|---|---|---|---|
| 2 | 7.94-7.86 (m, 3H), 7.80-7.72 (m, 5H), 7.66-7.42 (m, 5H), 7.38-7.15 (m, 8H), 7.05 (dd, 2H), 7.00 (dd, 2H) | 536.8 | 535.19 |
| 5 | 7.92-7.88 (m, 3H), 7.82-7.78 (m, 4H), 7.72-7.42 (m, 6H), 7.40-7.20 (m, 7H), 7.07 (dd, 12H), 7.02 (dd, 2H) | 510.1 | 509.18 |
| 10 | 7.92-7.89 (m, 3H), 7.80-7.76 (m, 5H), 7.74-7.50 (m, 5H), 7.48-7.44 (m, 5H), 7.27 (dd, 3H), 7.10 (dd, 1H) | 566.1 | 565.15 |
| 12 | 7.90-7.86 (m, 3H), 7.82-7.76 (m, 6H), 7.72 (dd, 4H), 7.67-7.50 (m, 6H), 7.42 (m, 3H) | 550.2 | 549.17 |
| 13 | 7.88-7.84 (m, 3H), 7.82-7.78 (m, 4H), 7.72-7.68 (m, 5H), 7.64-7.56 (m, 6H), 7.42 (m, 3H) | 476.7 | 475.61 |
| 20 | 7.92-7.60 (m, 11H), 7.58-7.48 (m, 7H), 7.42-7.25 (m, 4H), 7.20 (d, 1H), 1.86 (d, 6H) | 592.3 | 591.20 |
DEVICE MANUFACTURING EXAMPLES
Organic electroluminescence devices of Examples 1 to 6 were manufactured using Compounds 2, 5, 10, 12, 13 and 20 as materials for a light absorption layer.
[Example Compounds]
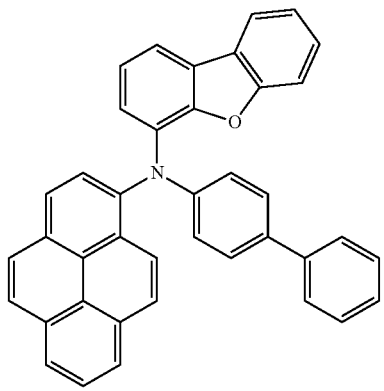
2
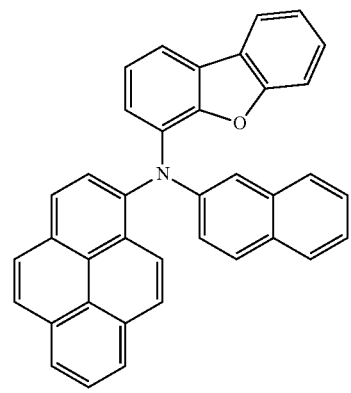
5
-continued
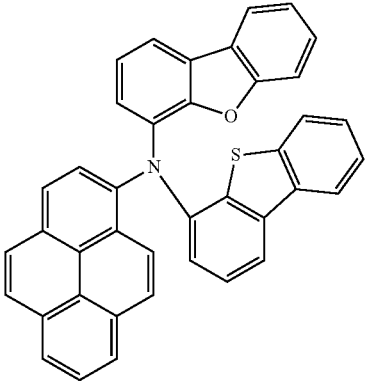
10
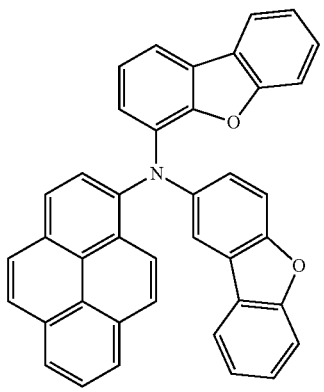
12

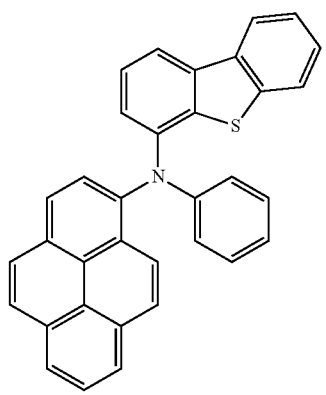

minutes, exposed to ozone for washing and installed in a vacuum deposition apparatus. On the ITO glass substrate, 2-TNATA was vacuum deposited first to form a hole injection layer to a thickness of about 600 Å, and on the hole injection layer, 4,4'-bis[N-(1-naphthyl)-N-phenylamino]biphenyl (hereinafter, NPB) was vacuum deposited to a thickness of about 300 Å to form a hole transport layer. On the hole transport layer, a blue fluorescent host ADN and a blue fluorescent dopant TPD were co-deposited in a weight ratio of 98:2 to form an emission layer to a thickness of about 300 Å. On the emission layer, $Alq_3$ was deposited to form an electron transport layer to a thickness of about 300 Å, and on the electron transport layer, LiF was deposited to form an electron injection layer to a thickness of about 10 Å. On the electron injection layer. Al was vacuum deposited to form a second electrode with a LiF/Al structure to a thickness of about 100 Å. On the second electrode, an example compound or a comparative compound was deposited to form a light absorption layer to a thickness of about 800 Å.

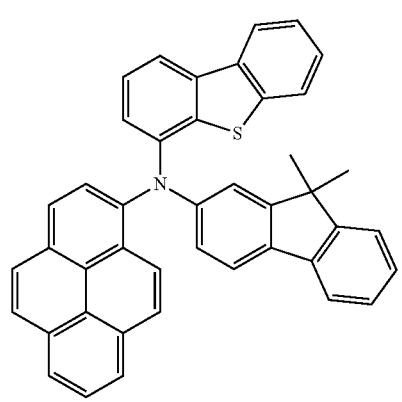

An organic electroluminescence device of Comparative Example 1 was manufactured using the following Comparative Compound, N,N'-di(1-naphthyl)-N,N'-diphenyl-(1,1'-biphenyl)-4,4'-diamine (NPB), as a material of a light absorption layer.

[Comparative Compound]

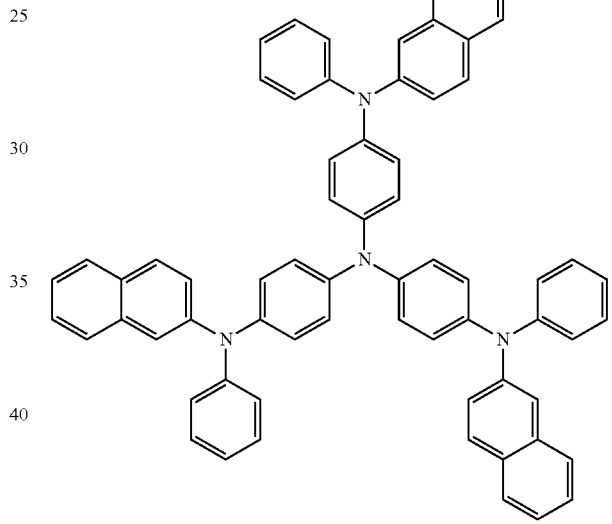

2-TNATA

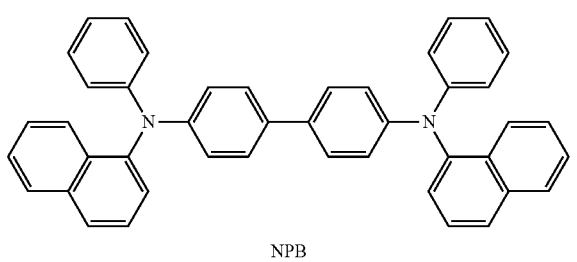 [SMILES: c1ccc(N(c2ccc(-c3ccc(N(c4ccccc4)c4cccc5ccccc45)cc3)cc2)c2cccc3ccccc23)cc1 ; "NPB"]

NPB

The organic electroluminescence devices of Examples 1 to 6 and Comparative Example 1 were manufactured as follows.

An ITO glass substrate (product of Corning Co.) on which an ITO layer with a thickness of 15 $\Omega/cm^2$ (1,200 Å) was formed, was cut to a size of 50 mm×50 mm ×0.7 mm, and was washed using isopropyl alcohol and pure water for about 5 minutes each using ultrasonic wave. Then, the ITO glass substrate was exposed to ultraviolet rays for about 30

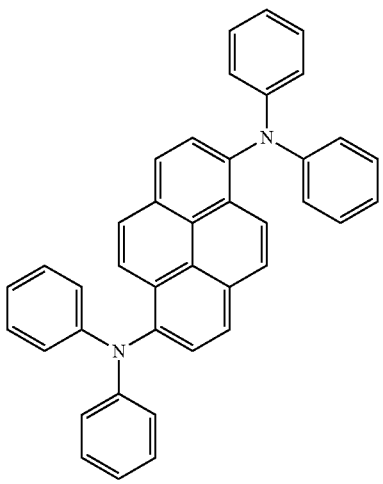

TPD

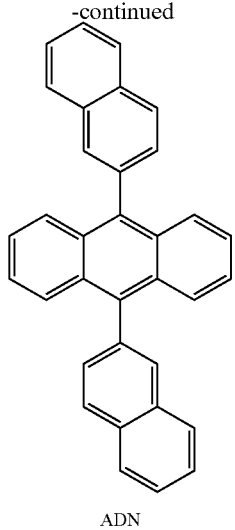

ADN

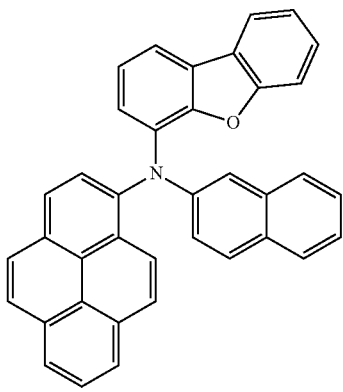

TABLE 2

| | Light absorption layer | Driving voltage (V) | Current density (mA/cm$^2$) | Luminance (cd/m$^2$) | Efficiency (cd/A) | Half life (hr @100 mA/cm$^2$) |
|---|---|---|---|---|---|---|
| Example 1 | Example Compound 2 | 5.90 | 50 | 2160 | 4.32 | 250 |
| Example 2 | Example Compound 5 | 5.92 | 50 | 2360 | 4.72 | 260 |
| Example 3 | Example Compound 10 | 5.88 | 50 | 2345 | 4.69 | 270 |
| Example 4 | Example Compound 12 | 5.76 | 50 | 2490 | 4.98 | 265 |
| Example 5 | Example Compound 13 | 5.90 | 50 | 2350 | 4.70 | 262 |
| Example 6 | Example Compound 20 | 5.92 | 50 | 2410 | 4.82 | 260 |
| Comparative Example 1 | Comparative Compound NPB | 5.94 | 50 | 2440 | 4.88 | 272 |

Figure 6:
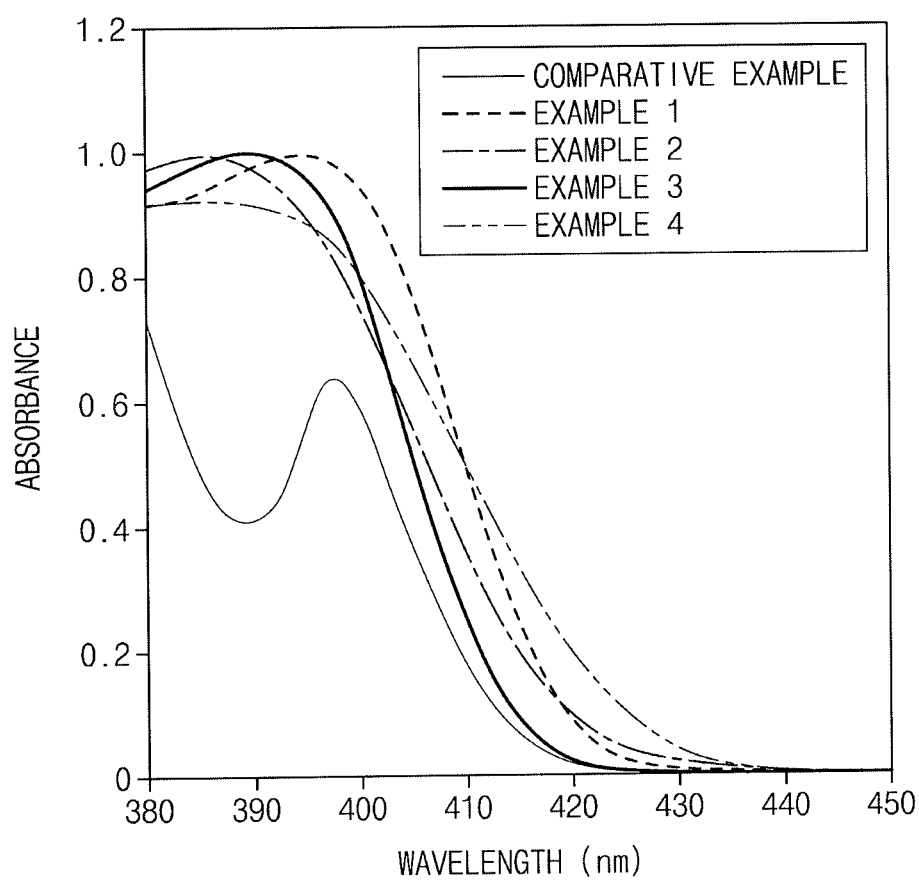
FIG. 6 is a graph illustrating light absorbance with respect to wavelength of example and comparative compounds.

FIG. 6 is a graph illustrating absorbance with respect to a wavelength region of example and comparative compounds. Particularly, FIG. 6 is a graph illustrating absorbance with respect to a wavelength region of Example Compounds 2, 5, 15 and 20 and the above-described Comparative Compound NPB.

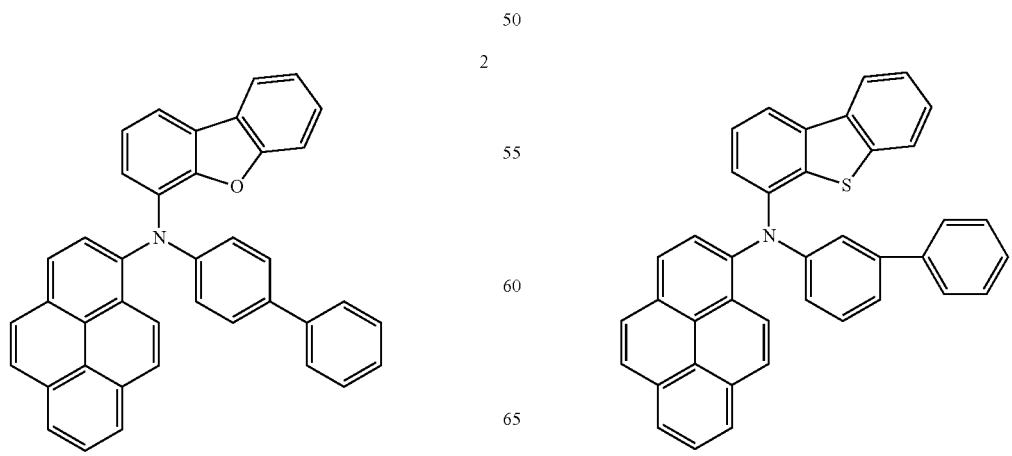

-continued

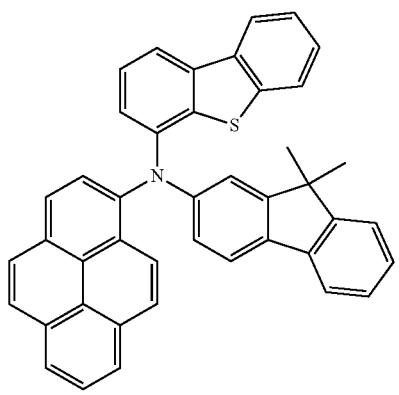

Referring to Table 2 and FIG. 6, it may be found that the light absorber according to an example embodiment has high light absorbance in a specific wavelength region (for example, from about 380 nm to about 420 nm), and an organic electroluminescence device in which a light absorption layer using the light absorber is applied has improved efficiency, life, etc. by preventing deterioration due to external light.

By way of summation and review, an organic electroluminescence device may be deteriorated by exposure to ultraviolet rays, for example, during a manufacturing process or exposure to the light of the sun due to outdoor use.

As described above, embodiments are directed to a light absorber including a pyrenyl group and an organic electroluminescence device including a light absorption layer including the absorber. The light absorber may provide excellent light absorbance with respect to ultraviolet rays and a portion of visible rays, and an organic electroluminescence device in which a light absorption layer using the light absorber is applied may exhibit improved efficiency, life, etc. by efficiently preventing deterioration due to external light. The light absorber may provide an excellent absorption rate of a portion of visible rays and ultraviolet rays.

The organic electroluminescence device including the light absorber according to an example embodiment may efficiently block the inflow of ultraviolet rays and a portion of visible rays into an emission layer, thereby improving stability, efficiency and life properties.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. An organic electroluminescence device, comprising:
a first electrode;
a hole transport region provided on the first electrode;
an emission layer provided on the hole transport region;
an electron transport region provided on the emission layer;
a second electrode provided on the electron transport region; and
a light absorption layer provided on at least one of a lower part of the first electrode or an upper part of the second electrode,
wherein the light absorption layer includes a monoamine compound represented by the following Formula 1, the monoamine compound being a light absorber:

[Formula 1]

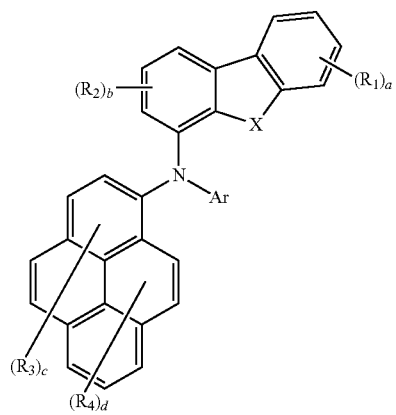

wherein in Formula 1,

X is O or S,

Ar is a substituted or unsubstituted aryl group having 6 to 30 carbon atoms for forming a ring, a substituted or unsubstituted heteroaryl group having 2 to 30 carbon atoms for forming a ring, or a substituted or unsubstituted condensed polycyclic group having 6 to 30 carbon atoms for forming a ring, $R_1$ to $R_4$ are each independently a hydrogen atom, a deuterium atom, a substituted or unsubstituted alkyl group having 1 to 10 carbon atoms, a substituted or unsubstituted aryl group having 6 to 30 carbon atoms for forming a ring, a substituted or unsubstituted heteroaryl group having 2 to 30 carbon atoms for forming a ring, or a substituted or unsubstituted condensed polycyclic group having 6 to 30 carbon atoms for forming a ring, "a" and "c" are each independently an integer of 0 to 4, "b" is an integer of 0 to 3, and "d" is an integer of 0 to 5, and wherein the first electrode and the second electrode are outmost electrode of the organic electroluminescence device.

2. The organic electroluminescence device as claimed in claim 1, wherein Formula 1 is represented by the following Formula 1-1:

[Formula 1-1]

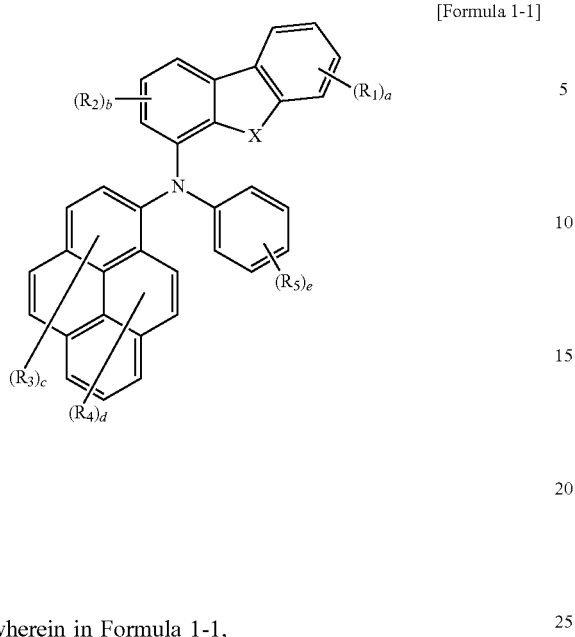

[Compound Group 1]

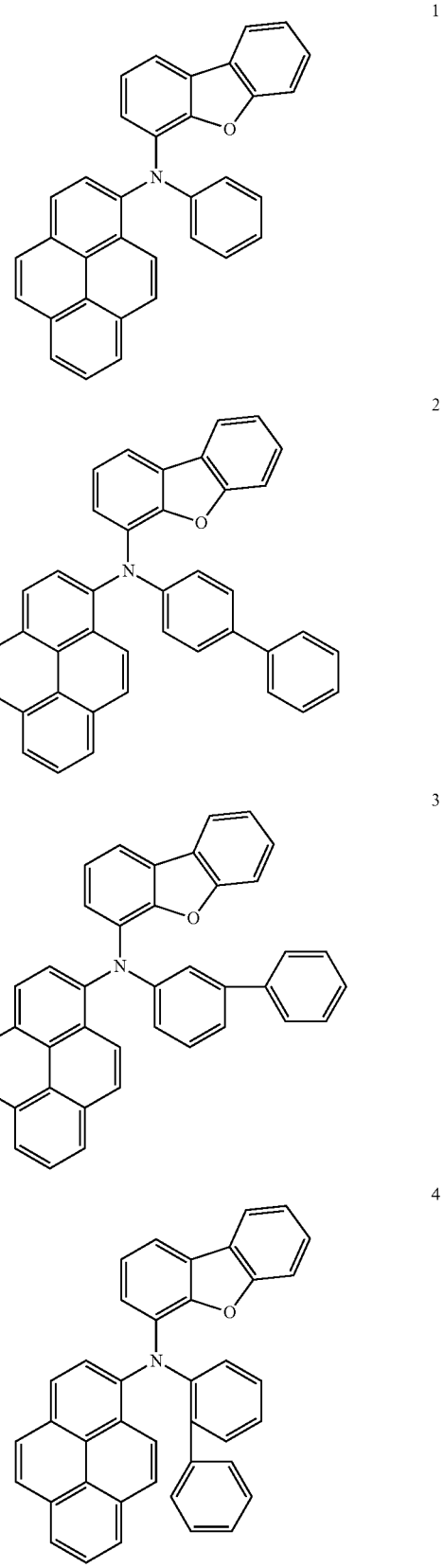

wherein in Formula 1-1, $R_5$ is a hydrogen atom, a deuterium atom, a substituted or unsubstituted alkyl group having 1 to 10 carbon atoms, a substituted or unsubstituted aryl group having 6 to 30 carbon atoms for forming a ring, a substituted or unsubstituted heteroaryl group having 2 to 30 carbon atoms for forming a ring, or a substituted or unsubstituted condensed polycyclic group having 6 to 30 carbon atoms for forming a ring, "e" is an integer of 0 to 5, in case "e" is 2 or more, adjacent $R_5$ groups are separate or are combined with each other to form a ring, and X, $R_1$ to $R_4$, and "a" to "d" are the same as defined in claim 1.

3. The organic electroluminescence device as claimed in claim 1, wherein Ar is a substituted or unsubstituted phenyl group, a substituted or unsubstituted biphenyl group, a substituted or unsubstituted naphthyl group, a substituted or unsubstituted fluorene group, a substituted or unsubstituted dibenzofuran group, or a substituted or unsubstituted dibenzothiophene group.

4. The organic electroluminescence device as claimed in claim 1, wherein the light absorber has a maximum absorption wavelength of about 380 nm to about 410 nm.

5. The organic electroluminescence device as claimed in claim 1, wherein the light absorption layer is provided on the second electrode and makes contact with the second electrode.

6. The organic electroluminescence device as claimed in claim 1, wherein the light absorption layer is a thin film encapsulation layer covering the first electrode, the hole transport region, the emission layer, the electron transport region and the second electrode.

7. The organic electroluminescence device as claimed in claim 1, wherein the light absorber represented by Formula 1 is at least one selected from compounds represented in the following Compound Group 1:

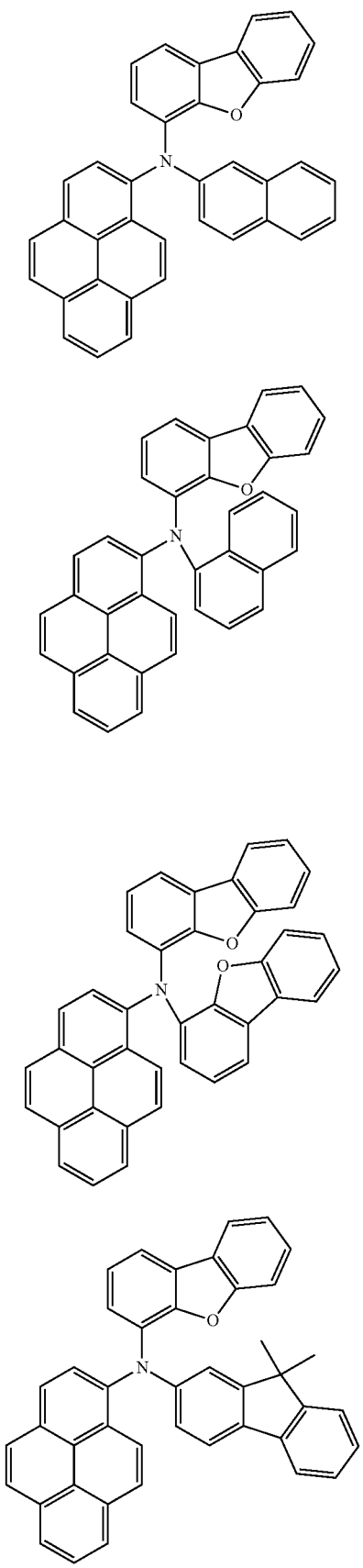
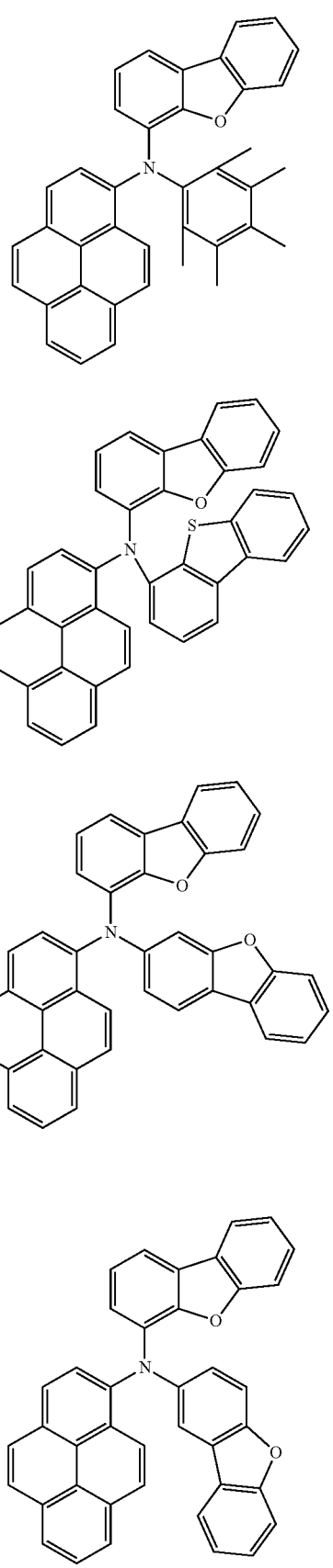

-continued
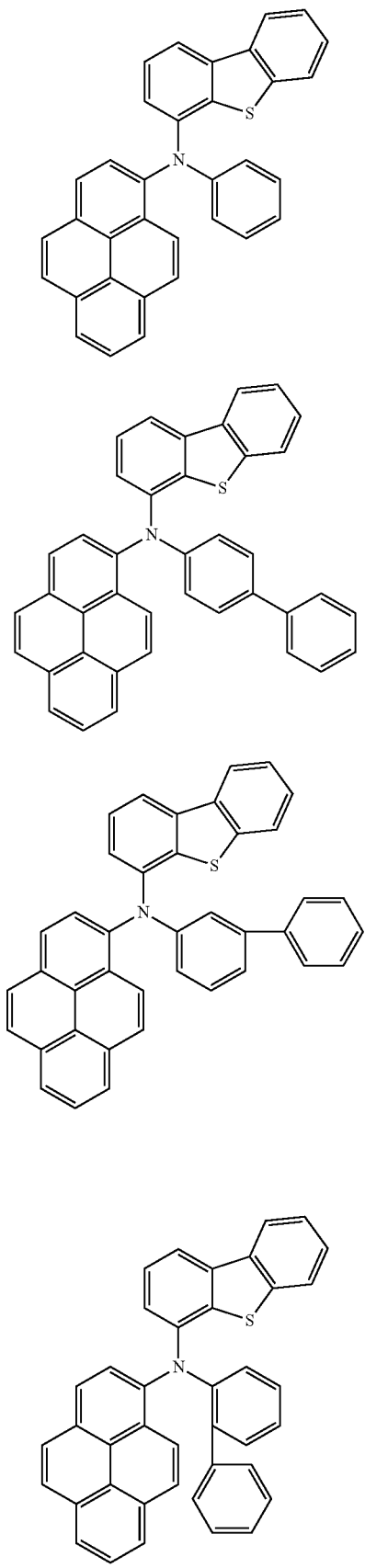
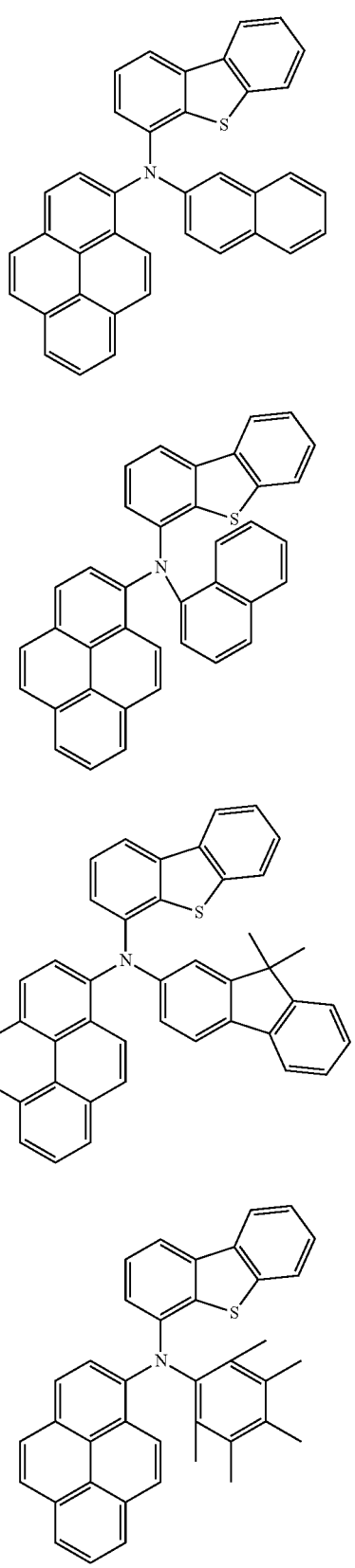

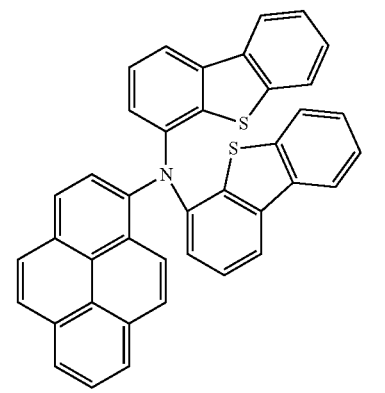

22

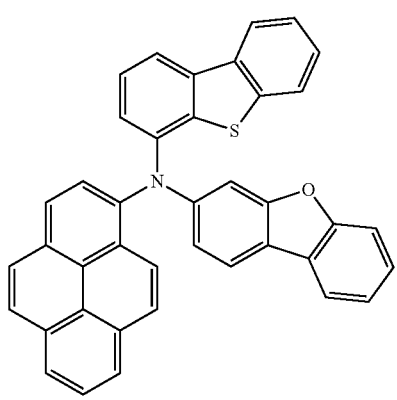

23

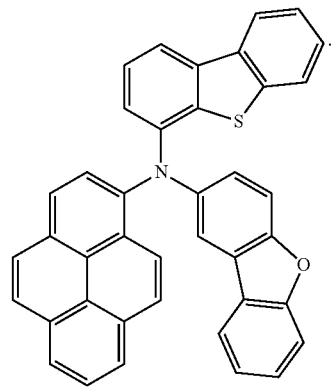

24

8. An organic electroluminescence device, comprising:
a first electrode;
a hole transport region provided on the first electrode;
an emission layer provided on the hole transport region;
an electron transport region provided on the emission layer;
a second electrode provided on the electron transport region; and
a light absorption layer provided on at least one of a lower part of the first electrode or an upper part of the second electrode,
wherein the light absorption layer includes a pyrenyl-substituted monoamine compound that absorbs light, and
wherein the first electrode and the second electrode are outmost electrode of the organic electroluminescence device.

9. The organic electroluminescence device as claimed in claim 8, wherein the pyrenyl-substituted monoamine compound is further substituted with at least one of a substituted or unsubstituted dibenzofuran group or a substituted or unsubstituted dibenzothiophene group.

10. The organic electroluminescence device as claimed in claim 9, wherein the pyrenyl-substituted monoamine compound is further substituted with a substituted or unsubstituted aryl group having 6 to 30 carbon atoms for forming a ring, a substituted or unsubstituted heteroaryl group having 2 to 30 carbon atoms for forming a ring, or a substituted or unsubstituted condensed polycyclic group having 6 to 30 carbon atoms for forming a ring.

11. The organic electroluminescence device as claimed in claim 9, wherein the pyrenyl-substituted monoamine compound is further substituted with a substituted or unsubstituted phenyl group, a substituted or unsubstituted biphenyl group, a substituted or unsubstituted naphthyl group, a substituted or unsubstituted fluorene group, a substituted or unsubstituted dibenzofuran group, or a substituted or unsubstituted dibenzothiophene group.

12. The organic electroluminescence device as claimed in claim 8, wherein the pyrenyl-substituted monoamine compound has a maximum absorption wavelength of about 380 nm to about 410 nm.

13. The organic electroluminescence device as claimed in claim 8, wherein the pyrenyl-substituted monoamine compound is at least one selected from compounds represented in the following Compound Group 1:

[Compound Group 1]

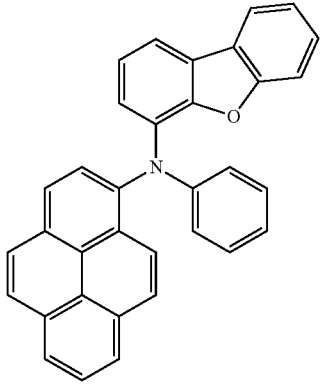

1

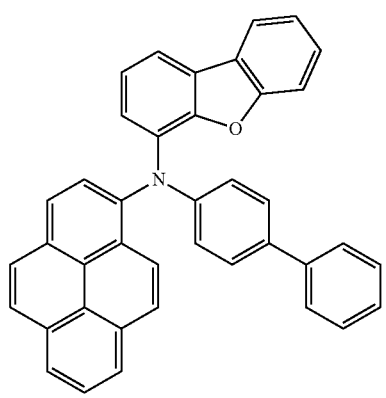

2

3
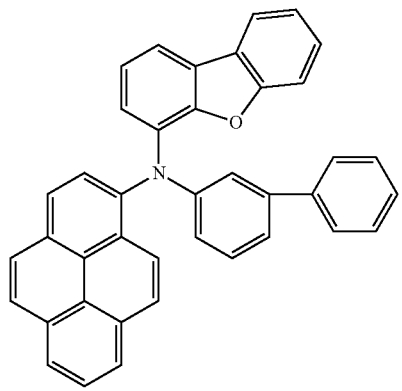
4
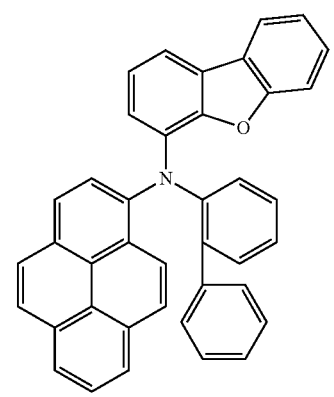
5
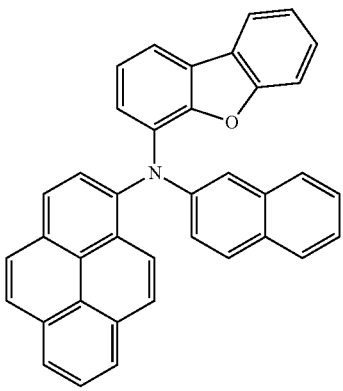
6
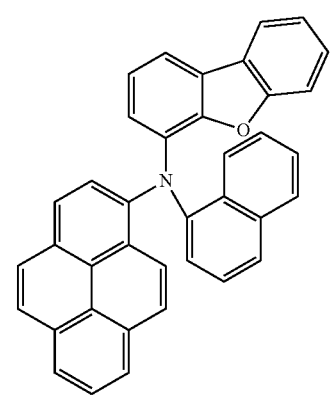
7
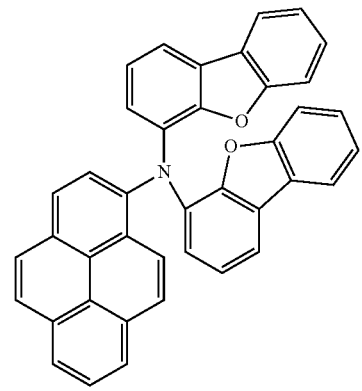
8
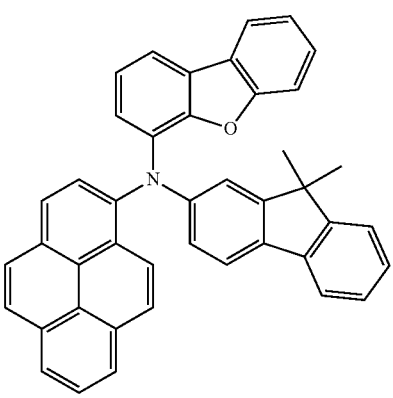
9
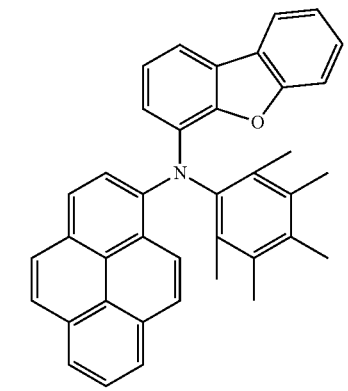
10
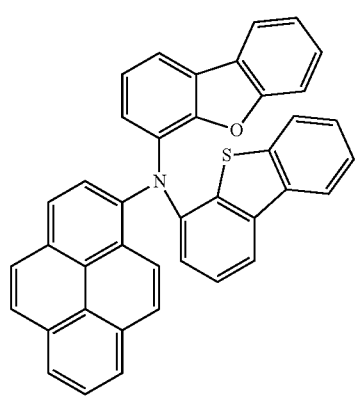

11
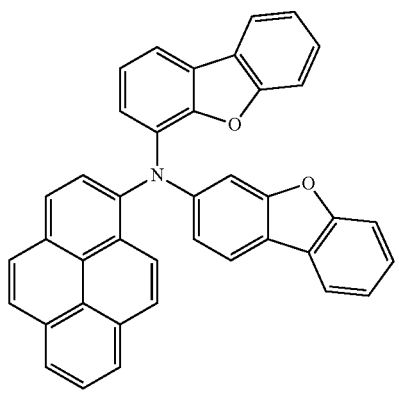
12
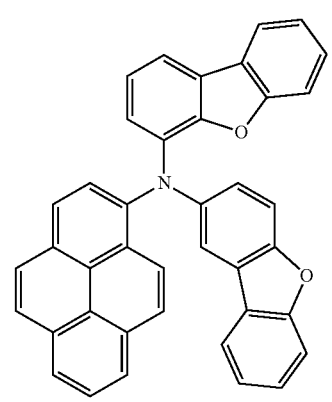
13
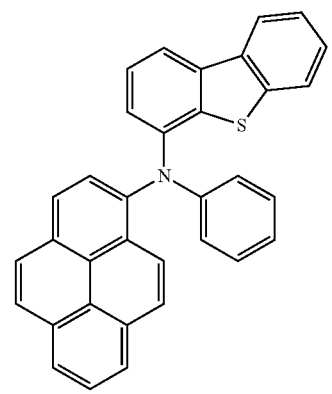
14
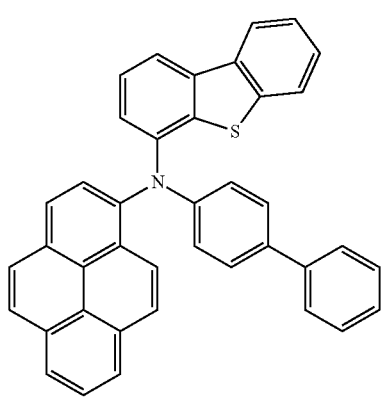
15
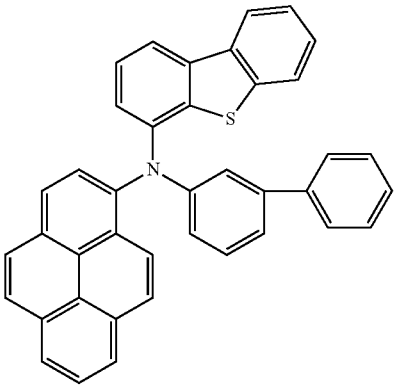
16
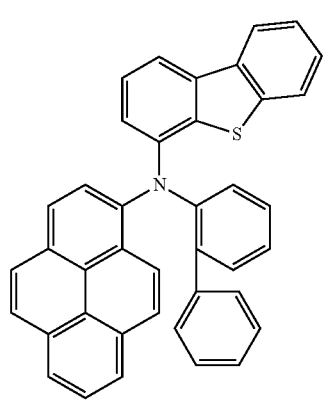
17
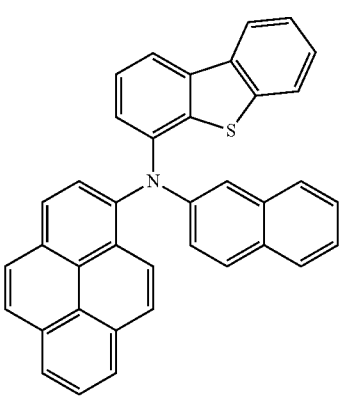
18
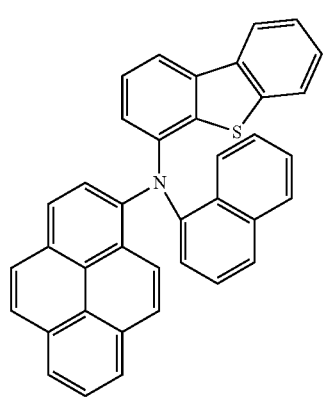

20 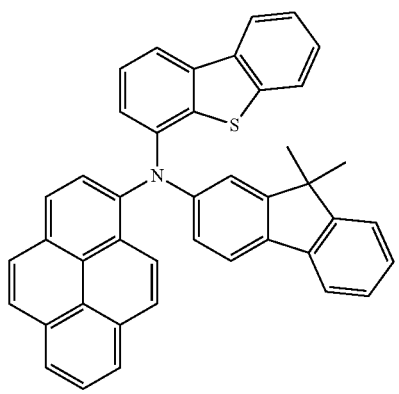
23 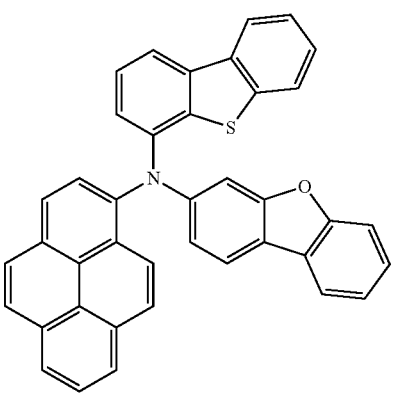
21 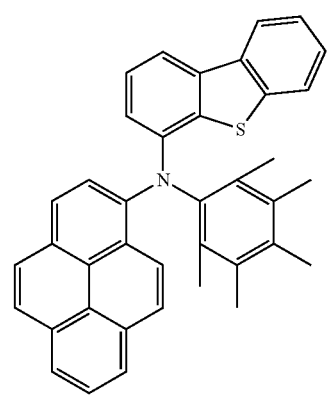
22 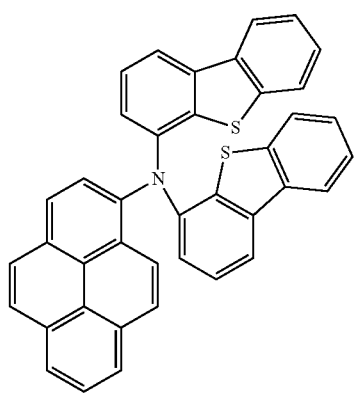
24 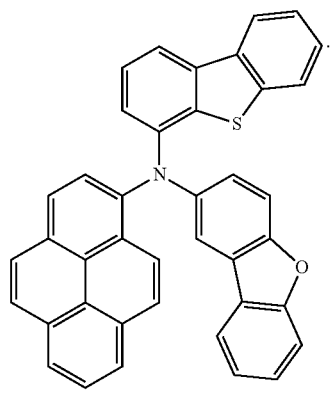
* * * * *